US011633511B2

(12) United States Patent
Clack et al.

(10) Patent No.: US 11,633,511 B2
(45) Date of Patent: *Apr. 25, 2023

(54) PRODUCTION OF IMMUNE-RESPONSE-STIMULATING AEROSOLS BY NON-THERMAL PLASMA TREATMENT OF AIRBORNE PATHOGENS

(71) Applicant: THE REGENTS OF THE UNIVERSITY OF MICHIGAN, Ann Arbor, MI (US)

(72) Inventors: Herek L. Clack, Ann Arbor, MI (US); Krista R. Wigginton, Ann Arbor, MI (US); Adam S. Lauring, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 861 days.

This patent is subject to a terminal disclaimer.

(21) Appl. No.: 16/509,724

(22) Filed: Jul. 12, 2019

(65) Prior Publication Data

US 2020/0016286 A1     Jan. 16, 2020

Related U.S. Application Data

(60) Provisional application No. 62/697,445, filed on Jul. 13, 2018.

(51) Int. Cl.
| | |
|---|---|
| *A61K 41/10* | (2020.01) |
| *A61L 2/14* | (2006.01) |
| *A61L 9/22* | (2006.01) |
| *F24F 3/16* | (2021.01) |
| *F24F 8/30* | (2021.01) |
| *H05H 1/26* | (2006.01) |

(52) U.S. Cl.
CPC .............. *A61L 2/14* (2013.01); *A61K 41/10* (2020.01); *A61L 9/22* (2013.01); *F24F 3/16* (2013.01); *F24F 8/30* (2021.01); *C12N 2710/00* (2013.01); *H05H 1/26* (2013.01); *H05H 2240/20* (2013.01)

(58) Field of Classification Search
CPC ..................................................... A61K 41/10
See application file for complete search history.

(56) References Cited

U.S. PATENT DOCUMENTS

| | | |
|---|---|---|
| 4,954,320 A | 9/1990 | Birmingham et al. |
| 5,843,288 A | 12/1998 | Yamamoto |
| 6,146,599 A | 11/2000 | Ruan et al. |
| 6,878,349 B2 | 4/2005 | Bianco et al. |
| 8,097,072 B1 | 1/2012 | Taylor |
| 9,572,241 B1 | 2/2017 | Eckert et al. |
| 11,179,490 B2 * | 11/2021 | Clack ...................... H05H 1/48 |
| 2003/0098230 A1 | 5/2003 | Carlow et al. |
| 2009/0274592 A1 | 11/2009 | Bergeron |
| 2017/0094769 A1 | 3/2017 | Eckert et al. |

FOREIGN PATENT DOCUMENTS

| | | |
|---|---|---|
| CN | 1691966 A | 11/2005 |
| CN | 104415659 A | 3/2015 |
| DE | 202012010239 U1 | 12/2012 |
| DE | 102015215051 A1 | 2/2017 |
| GB | 2524009 A | 9/2015 |
| WO | 2011123512 A1 | 10/2011 |

OTHER PUBLICATIONS

Wang et al, Non-thermal plasma for inactivated-vaccine preparation, Vaccine, 2016, vol. 34, pp. 1126-1132. (Year: 2016).*
Vladimir Scholtz, Jarmila Pazlarovab, Hana Souskovac, Josef Khuna, Jaroslav Julakd. Nonthermal plasma—A tool for decontamination and disinfection, Nov. 1, 2015, Biotechnology Advances, vol. 33(6)Part2; 1108-1119.
Beate Haertel, Thomas von Woedtke, Klaus-Dieter Weltmann, and Ulrike Lindequist. Non-Thermal Atmospheric-Pressure Plasma Possible Application in Wound Healing, Biomolecules & Therapeutics Nov. 2014; 22(6): 477-490.
Michel Ondarts, Wafa Hajjia, Jonathan Outina, Timea Bejatb, Evelyne Gonzea. Non-Thermal Plasma for indoor air treatment: Toluene degradation in a corona discharge at ppbv levels, Chemical Engineering Research and Design 2017; 118: 194-205.
Jung, Jae-Seung, Kim, Jin-Gyu. An indoor air purification technology using a non-thermal plasma reactor with multiple-wire-to-wire type electrodes and a fiber air filter. Journal of Electrostatics 2017; 86: 12-17.
Rasoul Yarahmadi, Sayed Bager Mortazavi, and Parvin Moridi. Development of Air Treatment Technology Using Plasma Method. International Journal of Occupational Hygeine, 2012; 4:27-35.
Nachiket D. Vaze, Sin Park, Ari D. Brooks, Alexander Fridman, Suresh G. Joshi. Involvement of multiple stressors induced by non-thermal plasma-charged aerosols during inactivation of airborne bacteria. PLOS One 2017, 12(2).

(Continued)

*Primary Examiner* — Mark Halvorson
*Assistant Examiner* — Dennis J Sullivan
(74) *Attorney, Agent, or Firm* — Harness, Dickey & Pierce, P.L.C.

(57) ABSTRACT

Infectious diseases can be transmitted to humans, or between humans and animals, by airborne viruses and bacteria, known as infectious aerosols. Current protective measures that individuals can take to avoid inhaling such aerosols are either marginally effective (personal face masks) or impractical (self-contained breathing apparatuses). Building ventilation systems employing high-efficiency filters to prevent distribution of such aerosols suffer from high energy costs and high filter replacement costs. The development of conventional, intramuscularly administered vaccines takes months or years to produce enough doses to protect a population from a rapidly spreading infectious disease. Airborne viruses and bacteria have been shown to be completely inactivated when exposed to non-thermal plasmas. Results indicate the potential for sub-lethal exposures of airborne pathogens could render them unable to spark an infection in a host, but still retain the necessary surface proteins to cause an immune response in the host.

7 Claims, 19 Drawing Sheets

(56) References Cited

OTHER PUBLICATIONS

Yan Wu, Yongdong Liang, Kai Wei, Wei Li, Maosheng Yao, Jue Zhang and Sergey A. Grinshpun. MS2 Virus Inactivation by Atmospheric-Pressure Cold Plasma Using Different Gas Carriers and Power Levels. Applied and Environmental Microbiology 2015; 81(3): 996-1002.

Huang, Yaohua, "Non-thermal Plasma Inactivation of Bacillus Amyloliquefaciens spores." Master's Thesis, University of Tennessee, 2011.

Herek Clack et al., "NIH Mechanism of Airborne Virus Inactivation" Narrative, 2018.

Herek Clack et al., "NSF CBET Non-thermal Plasma Oxidant Reactions with Viral Proteins" Project Narrative, 2017.

Next generation Non-Thermal Plasma Technology demonstrates effectiveness in the fight against tough infectious agents, Jan. 7, 2016, PR Newswire, ChiScan.

Rosocha, L. A. Non-Thermal Plasma Techniques for Air Treatment. Los Alamos National Laboratory, Los Alamos, NM, 1999.

https://www.youtube.com/watch?v=0jVyU93fYds, Air Purification with Cold Plasma, Frank Pels, Youtube, Jan. 19, 2012.

https://www.youtube.com/watch?v=srWjmZBcPZA, Aerox Technology—Non Thermal Plasma AeroxBV, Youtube, Nov. 16, 2012.

* cited by examiner

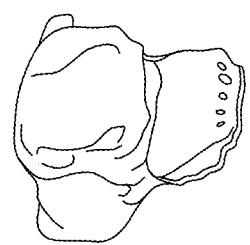
NTP-2 Min-NDV-Vaccine Group
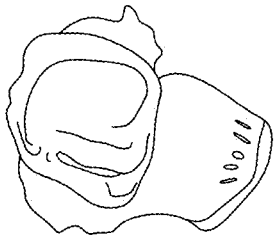

|  | Genome type | Genome size (b or bp) | Particle size (nm) | Enveloped/ Nonenveloped |
|---|---|---|---|---|
| Vesicular stomatitis virus | (−)ssRNA stomatitis virus | 11,000 | 70 x 200 | Enveloped |
| Bacteriophage Φ6 | dsRNA | 13,000 | 85 | Enveloped |
| Bacteriophage MS2 | (+)ssRNA | 3600 | 27 | Nonenveloped |
| PhiX174 | dsDNA | 5400 | 25 | Nonenveloped |

*Fig-18*

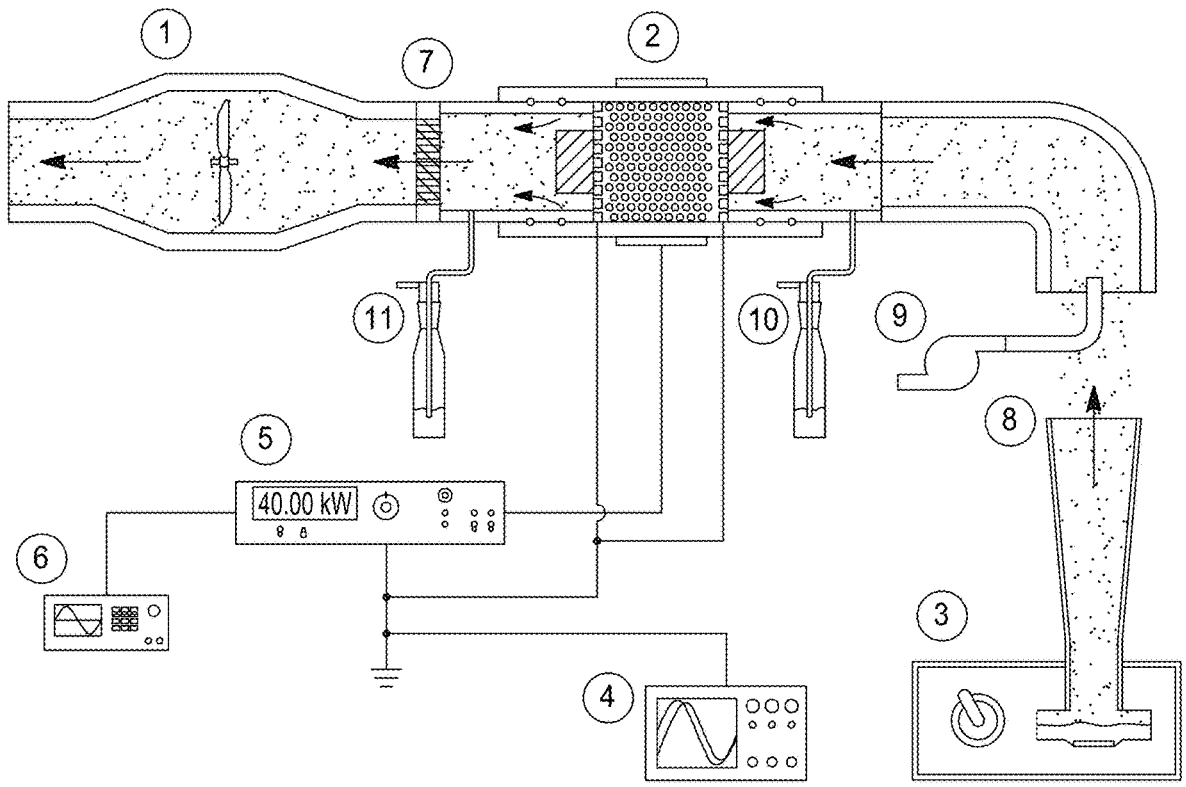

(1) In-line duct fan
(2) Dielectric Barrier Discharge (DBD) reactor
(3) Piezoelectric mist generator
(4) Digital oscilloscope
(5) High voltage amplifier
(6) Digital function generator
(7) In-line ozone filter
(8) Humidifier outlet
(9) Dried house compressed air
(10)

| Parameter | Value |
|---|---|
| Exposure time**, $O^*$, $O^-$, $OH^-$ | < 10 msec** |
| Exposure time, $O_3$, $NO/NO_2$ (+ROC) | Up to 3 sec |
| Temperature | 20-25 °C |
| Relative Humidity | 10-50% |
| $O_3$ concentration | < 100 ppb |
| $NO/NO_2$ concentration | < 500 ppb |
| ROC (limonene) concentration | 0, < 2 ppm |
| $O^*$, $O^-$, $OH^-$ concentrations | Inferred from Global_Kin |

Fig-20

PRODUCTION OF IMMUNE-RESPONSE-STIMULATING AEROSOLS BY NON-THERMAL PLASMA TREATMENT OF AIRBORNE PATHOGENS

CROSS-REFERENCE TO RELATED APPLICATIONS

This application claims the benefit of U.S. Provisional Application No. 62/697,445, filed on Jul. 13, 2018. The entire disclosure of the above application is incorporated herein by reference.

FIELD

The present disclosure relates to the production of immune-response-stimulating aerosols by non-thermal plasma treatment of airborne pathogens.

BACKGROUND AND SUMMARY

This section provides background information related to the present disclosure which is not necessarily prior art. This section provides a general summary of the disclosure, and is not a comprehensive disclosure of its full scope or all of its features.

Newcastle disease virus (NDV) and avian influenza virus (AIV) are two of the most important pathogens in poultry. Outbreaks of high-pathogenicity avian influenza have been reported as a threat to both humans and animals. Newcastle disease is usually caused by highly pathogenic NDV, which can result in 100% mortality in many species of birds worldwide. Thus, severe economic loss in the poultry industry caused by NDV and AIV highlights the importance of vaccines.

Generally there are three types of vaccines, i.e., conventional inactivated vaccines, live attenuated vaccines and gene-manipulated vaccines such as vectored viruses, subunit proteins and DNA vaccines. However, scaled-up production, cost and immune potency are issues that should be solved before commercial gene-manipulated vaccines reach the market. Additionally, in live attenuated vaccines, there are doubts about whether virulence remains. Currently, the most popular vaccine in poultry farming is still the conventional inactivated vaccine. Conventional inactivated vaccines usually rely on chemical reagents such as formaldehyde and ß-propiolactone. However, the kinetics of the formaldehyde inactivation process are not first-order. Formaldehyde is found to be associated with enhanced disease during subsequent infection. Moreover, residual formaldehyde and ß-propiolactone in the vaccines have mutagenic effects that are harmful to both animals and humans. For both consumers and farmers, an alternative technique that is safer, more effective and lower in cost is expected for inactivated vaccine preparation.

In recent years, non-thermal plasma (NTP) has been receiving sustained attention owing to its proven effectiveness in biomedical fields, such as bacterial sterilization, surface modification, and food preservation. The advantages of NTP are that it requires a low temperature, is environment-friendly and is free of toxicity. As for the mechanism of NTP, it has been well recognized that reactive oxygen species (ROS) and reactive nitrogen species (RNS) play key roles in its application, especially in its biomedical effects. According to the literature, a few studies have demonstrated the excellent inactivation effect of NTP on viruses such as adenoviruses, herpes simplex virus and MS2 bacteriophage.

In a study by Wang et al. (Wang G, Zhu R, Yang L, Wang K, Zhang Q, Su X, Yang B, Zhang J, Fang J. 2016. "Non-thermal plasma for inactivated-vaccine preparation". Vaccine 34:1126-1132), NTP was first used to inactivate NDV and AIV. Then the inactivated vaccines were prepared by following standard procedures, and serological tests were carried out in specific pathogen-free (SPF) chickens. Scanning electron microscopy (SEM) and transmission electron microscopy (TEM) were used to observe the morphological changes of the viruses before and after NTP treatment. Furthermore, the underlying mechanism of the NTP technology was investigated using oxidation-reduction potential (ORP) tests, pH measurements and antioxidant assays of the virus allantoic fluid, as well as optical emission spectrum (OES) analysis.

In order for viruses present in food or water, on solid surfaces, or as aerosols to result in disease transmission, they must survive these environments and reach their target cells in a new host in quantities exceeding the infectious dose. Virus structure and morphology are observed as influencing virus survival in the environment, although a mechanistic understanding remains elusive. For example, the time required for inactivation of 90% of viruses ($T_{90}$) in buffer or media ranges from days to months for nonenveloped viruses as compared to hours to days for enveloped viruses under the same temperature conditions. In aqueous environments, inactivation mechanisms are emerging. For viruses exposed to chemical oxidants in water, key factors include the numbers of methionine and cysteine residues exposed on the surface of viral proteins. For solar UV and germicidal UV, genome type and virus length are important, as is the association of the genome with key proteins.

Much less is known about the mechanisms of virus inactivation in air and how virus survival in aerosols ultimately impacts disease transmission. Weber and Stilianakis reviewed the environmental factors influencing influenza A transmission which, for the airborne transmission route, included temperature, relative humidity, UV irradiation, and chemical oxidants. The role of chemical oxidants involved in aerosol virus inactivation is arguably the most poorly understood. Early observations by May et al. found 10 to 100 times faster loss of $E.\,coli$ viability in nighttime outside air than in clean laboratory air. This so-called "open air factor", OAF was ultimately attributed to the oxidants formed from reactions between ozone (O3) and a variety of double-bonded (C=C) reactive organic compounds (ROCs). Less potent oxidants such as NO/NO2 appear to further enhance this effect. Ozone, NO/NO2 and ROCs are common components of ambient outdoor air, and indoor environments also contain various sources of ozone (office equipment), NO/NO2 (combustion sources), and ROCs (fragrances, cleaning products, interior finishes) that have been shown in indoor air chamber tests to promote formation of a variety of other oxidants.

Mechanistic models of virus inactivation in air are needed. Such models would explain why some viruses more than others remain viable in the atmosphere long enough to infect new hosts. Such models would be useful when applied to emerging viruses or viruses that lack readily available cell culture systems.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1A is a schematic diagram of a NTP system and a process of plasma treatment.

FIG. 1B is an experimental procedure description in connection with FIG. 1A (OES, optical emission spectrum; ORP, oxidation-reduction potential; SPF, specific pathogen free; ELA, embryo lethality analysis; HA test, hemagglutination test; NDV, Newcastle disease virus; AIV avian influenza virus).

FIG. 4B shows the typical clinical signs and gross lesions at necropsy after challenge with virulent NDV.

FIG. 8 is a comparison of demonstrated NTP inactivation of MS2 phage and PRRSv aerosols in air.

FIG. 9 is a size-dependent aerosol trajectories within wire-plate NTP.

FIG. 12A shows φ6 genome decay during exposure to free chlorine, leading to inactivation.

FIG. 12B shows φ6 genome decay during exposure to ultraviolet, leading to inactivation.

FIG. 13 is a schematic of NTP flow reactor and experimental apparatus.

FIGS. 16A-D are predictions from Global_Kin for reactive species in a humid air plasma produced by 5000 pulses in a dielectric barrier discharge, reactive oxygen species, and reactive nitrogen species.

Figure 17:
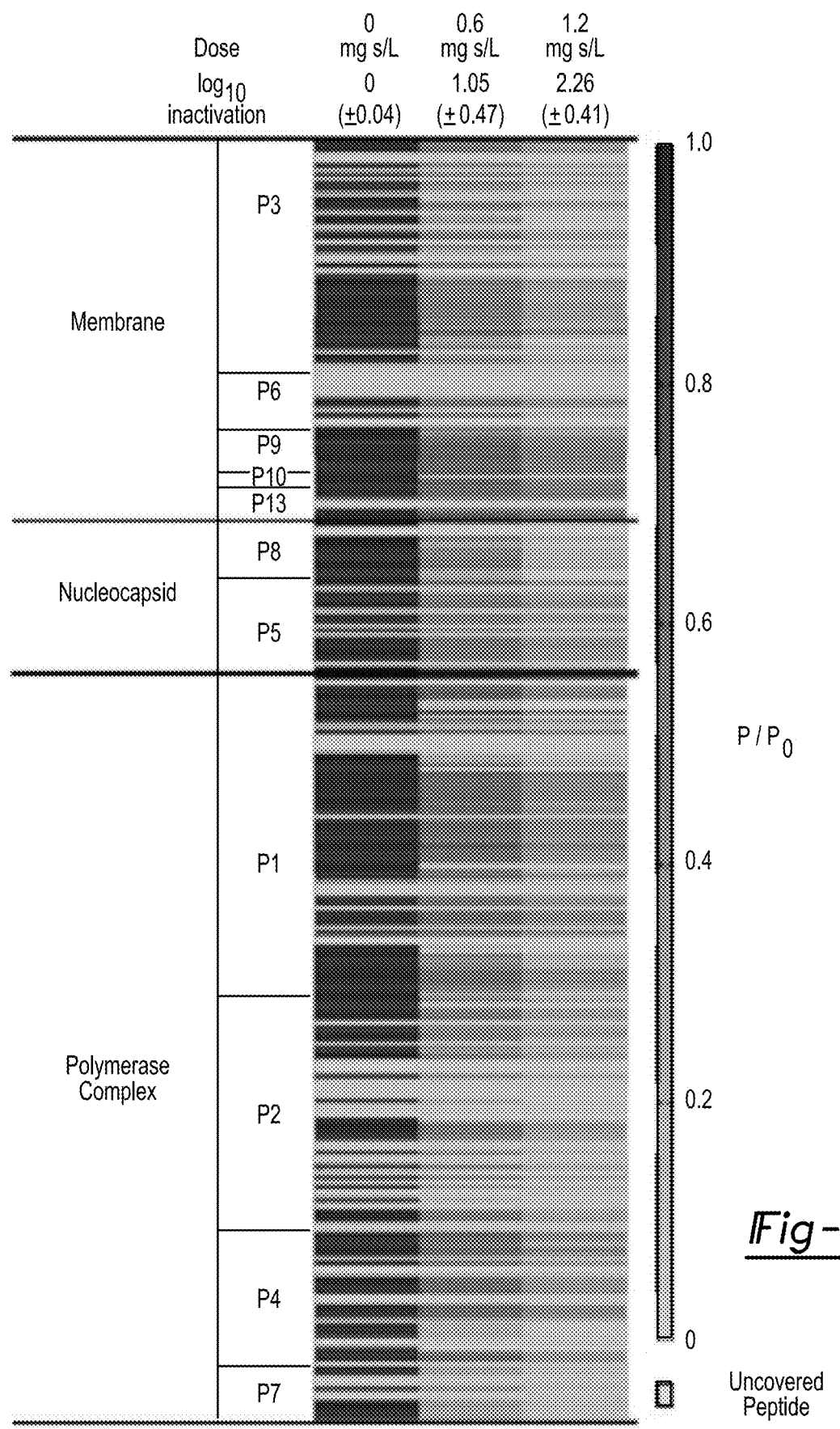

FIG. 17 is a heat plot of φ6 protein peptide reactivity with free chlorine measured with high resolution mass spectrometry.

FIG. 18 is a table of model viruses included in this study.

FIG. 19 is a schematic of experimental apparatus used for viral aerosol exposure to oxidizing environments.

FIG. 20 is a table of experimental conditions of viral aerosol exposure to oxidants.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

According to the principles of the present teachings, the inventors have been at the forefront of probing inactivation mechanisms of non-enveloped viruses in aqueous environments. Combining molecular methods, traditional culture-based methods, and high-resolution mass spectrometry to link virus inactivation to specific structural features (see FIG. 17). Their work has demonstrated that environmental stressors target specific regions of the virus particle; a virus that is easily inactivated by temperature may, in fact, withstand exposure to relatively high levels of oxidants.

Recent work by the inventors has expanded to include enveloped virus fate in aqueous systems. Thus far, their work has demonstrated that in municipal wastewater, enveloped viruses will associate to a greater extent with biosolids than non-enveloped viruses. Ye et al. identified the inactivating mechanisms of enveloped virus surrogate φ6 when exposed to oxidants and UV radiation in water. φ6 was particularly susceptible to inactivation by hypochlorous acid compared to nonenveloped viruses and the team linked the fast φ6 inactivation kinetics to reactive φ6 proteins (FIG. 17). Interestingly, the reaction kinetics of the fastest reacting peptides in φ6 proteins were ~150× faster than the reaction kinetics of fastest reacting peptides in nonenveloped virus peptides MS2, GA, and fr. Only minor modifications were detected in the virus lipid layer following up to 4-log inactivation by chlorine. Inactivation of the φ6 virus to UV254 was attributed entirely to genome damage.

Figure 7:
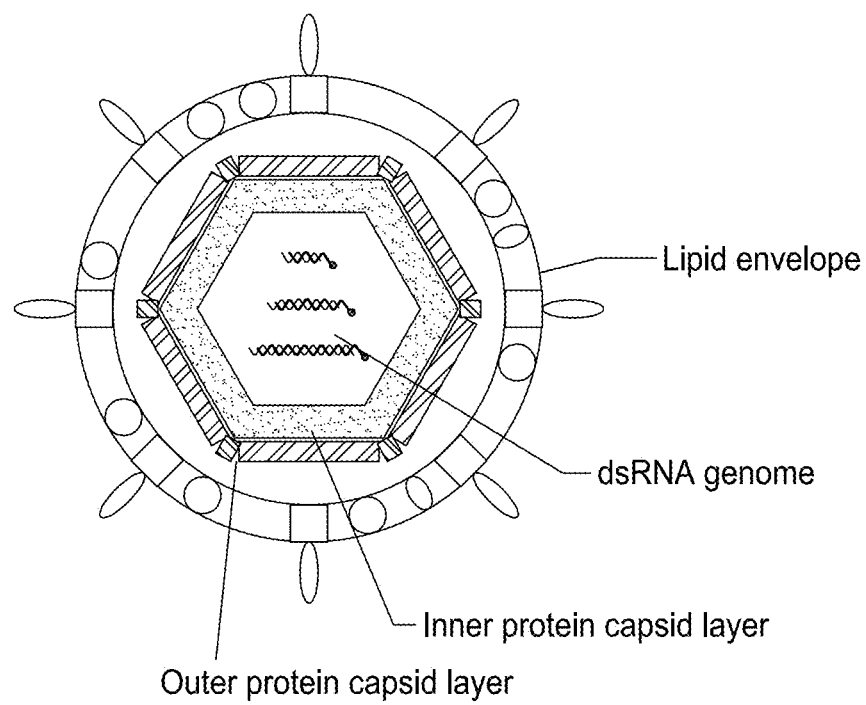
FIG. 7 is a structure of surrogate enveloped virus φ6.

Viral respiratory infections are a major contributor to global mortality rates and novel respiratory viruses regularly emerge. Of all acute illnesses in the developed world, approximately 75% are respiratory, and nearly 80% of these are viral. Several recent outbreaks in humans highlight this phenomenon, including the severe acute respiratory syndrome (SARS) coronavirus outbreak in 2003, the Middle Eastern respiratory syndrome (MERS) coronavirus outbreak, and the H5N1 and H1N1 influenza outbreaks. Meanwhile the viral disease of livestock present a large and increasing threat to agriculture and food security. In 2015, outbreaks of avian influenza (AI) caused U.S. poultry farmers to euthanize more than 40 million head of poultry. Porcine reproductive and respiratory syndrome (PRRS) virus is estimated to cost U.S. pork producers more than $1B annually and viable PRRS virus has been found in air up to four kilometers downwind of infected swine. The U.S. Department of Homeland Security estimates the cost of a single foreign animal disease outbreak to be $60B when the costs of response, animal depopulation, and trade embargoes are considered. These destructive, costly, and highly publicized outbreaks of human livestock diseases are caused by enveloped viruses. Enveloped viruses consist of an RNA or DNA genome encased within a protective protein capsid with a lipid envelope (see FIG. 7). Compared to nonenveloped viruses, enveloped viruses are considered to be more susceptible to oxidants and high humidity conditions, although little work on the mechanistic fate of enveloped viruses has been conducted.

In ambient air, multiple factors can promote the spontaneous inactivation of viruses including temperature, UV irradiation, chemical oxidation, and desiccation. Prior research has often focused on environmental factors in ambient air to explain, e.g., the seasonality of influenza outbreaks; Weber and Stilianakis provide a review of such efforts. Nevertheless, there remains substantial debate about the role each of these factors plays in determining the persistence and viability of viruses in air. Observed differences between field-measured and laboratory-measured persistence of airborne bacteria were originally attributed to an unspecified "open air factor", which has subsequently been determined to be the effect of additional oxidants produced in outdoor air as a result of reactions between ozone and trace amounts of C=C bonded gaseous compounds, For engineered air flows (ventilation), the inventors have quantified degrees of inactivation of both enveloped and nonenveloped viruses in flowing air streams exposed to the highly oxidizing environment of a non-thermal plasma (NTP). NTPs are stable electrical discharges that produce reactive species that depend on the carrier gas used; in ambient air, among the species NTPs produce are O*, OH—, and OH*, species that are orders of magnitude more reactive than ozone ($O_3$), NTPs have been used for biological treatment of surfaces such as food products, skin diseases, and promoting post-surgical wound healing. NTPs have also been studied and used to destroy gaseous chemical contaminants such as volatile organic compounds and nitrous and sulfurous oxides ($NO_x$ and $SO_x$) produced from combustion, However, the intersection of these two applications—biological disinfection of airstreams—has received much less attention. For applications in agriculture, NTP-based airstream sterilization presents far lower differential pressure than HEPA filtration and, unlike vaccines whose effectiveness declines as viruses mutate, the inactivation of NTPs is robust in the face of viral mutations.

Figures 8, 9:
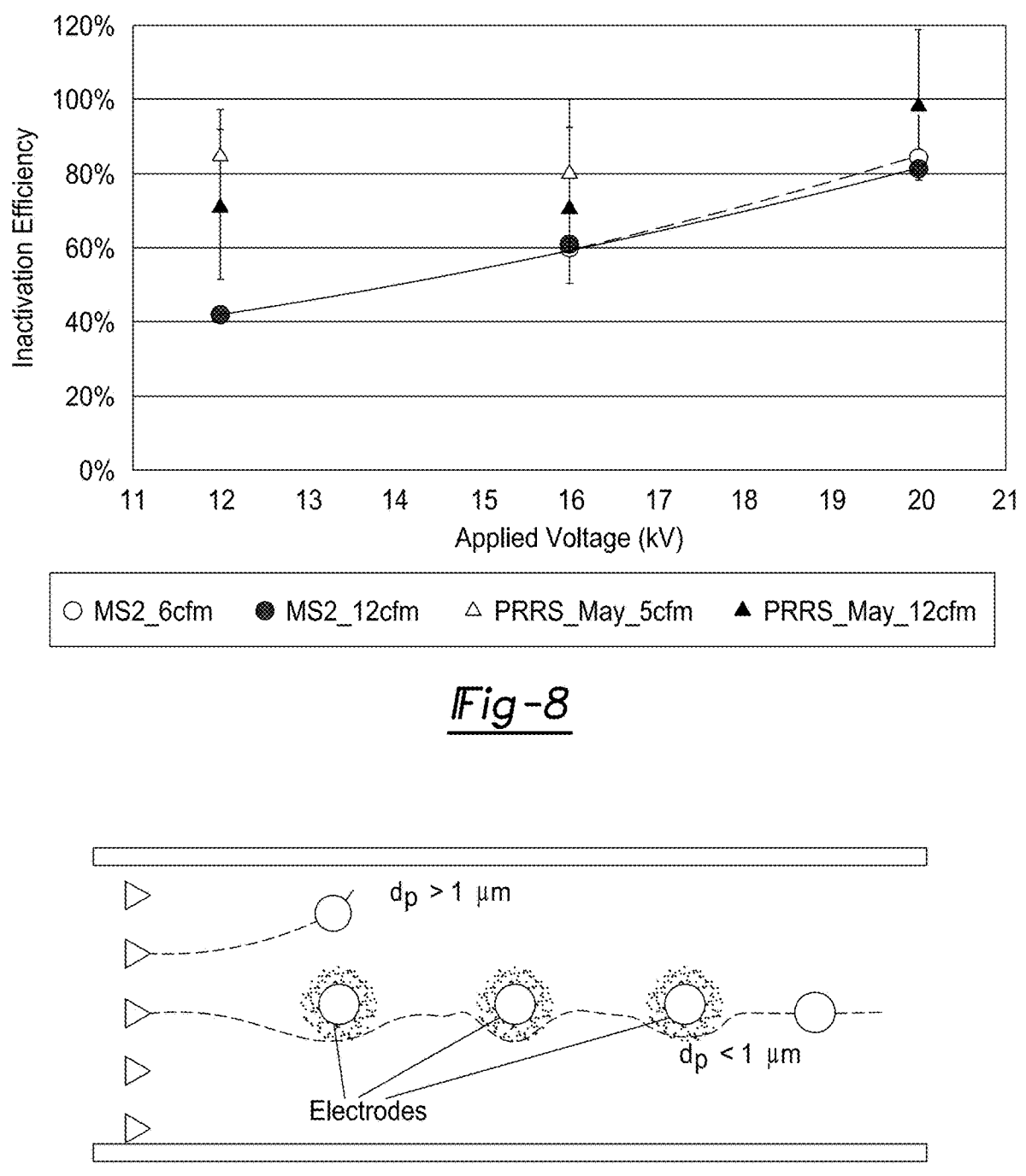

On this basis, the inventors have used an NTP flow reactor (depicted in FIG. 14 and schematized FIG. 13) to demonstrate effectiveness in inactivating both MS2 a nonenveloped single-stranded RNA virus, and PRRSv, an enveloped single-stranded RNA virus (in collaboration with M. Torremorell and B. Olson, Univ. of Minnesota). NTP inactivation NTP inactivation of MS2 ranged from about 60% at 12 kV to over 80% at 20 kV, as shown in FIG. 8, and consuming about 1.7 W of power. Halving the NTP exposure time by doubling the air flow rate from 170 to 330 slpm did not result in appreciable differences in inactivation, suggesting that applied power and availability of radical species were the performance-limiting factors. At the maximum of 30 kV (not shown in FIG. 2), MS2 inactivation was so thorough that it exceeded the quantification limit (Q.L.) for the method, i.e., no plaques were found to have formed in E. coli colonies inoculated with the most concentrated titer collected after NTP treatment. Conservatively assuming that the abundance of infective MS2 in post-NTP-treatment samples is just below the Q.L., these results indicate at least a 2.3 log reduction in infective MS2 by the NTP reactor at these conditions. Companion qPCR analyses at these conditions generally showed ~0.3 log reduction in genome copies across the reactor due to physical and electrostatic filtration. NTP inactivation of PRRSv at equivalent or nearly equivalent conditions was at least as effective as that demonstrated for MS2, as shown in FIG. 8.

Electro-hydrodynamic (EHD) phenomena are those effects produced when a strong electric field, such as that generated by a corona discharge type of NTP, exerts a Coulombic force within a fluid having sufficient concentrations of ions resulting in ion-driven fluid flows. EHD phenomena have been reported by other researchers, both experimentally and through simulations. Clack conceived of EHD-enhanced NTPs as an outgrowth of his research in gas-particle transport processes occurring within electrostatic precipitators (ESPs), which are large, widely used industrial emissions control devices for removing particulate matter. FIG. 9 is a conceptual representation of EHD-enhanced NTPs. For 2-D channel flows containing arrays of high-voltage wire electrodes, corona discharges are supported in the strong electric field above the surface of each wire. Viruses, bacteria, and particles bearing them that enter the channel follow fundamental principles of electrostatic precipitation: larger aerosols ($d_p > \sim 1$ μm) with greater charge drift at higher speeds towards the channel walls where they impact and adhere. Smaller aerosols (($d_p < \sim 1$ μm) with less charge drift more slowly and as a result follow fluid stream lines with greater fidelity and are transported into the corona in the near-wire region. Simulation of these flows requires solution of the coupled governing fluid dynamic equations (eqs. 1 and 2, Navier-Stokes equations), subject to the governing electric equations (eqs. 3 and 4, Poisson's equation and current continuity). Development of eqns 1-4 can be found below:

$$\rho(\nabla \cdot \vec{U}) = 0$$

$$\rho(\vec{U} \cdot \nabla \vec{U}) = -\nabla P + \mu \nabla^2 \vec{U} + q_i \nabla \Phi$$

$$\nabla^2 \Phi = -\frac{q_i}{\varepsilon}$$

$$\nabla \cdot ((b_i \nabla \Phi + \vec{u})q_i + \alpha \nabla q_i) = 0$$

Figure 10A:
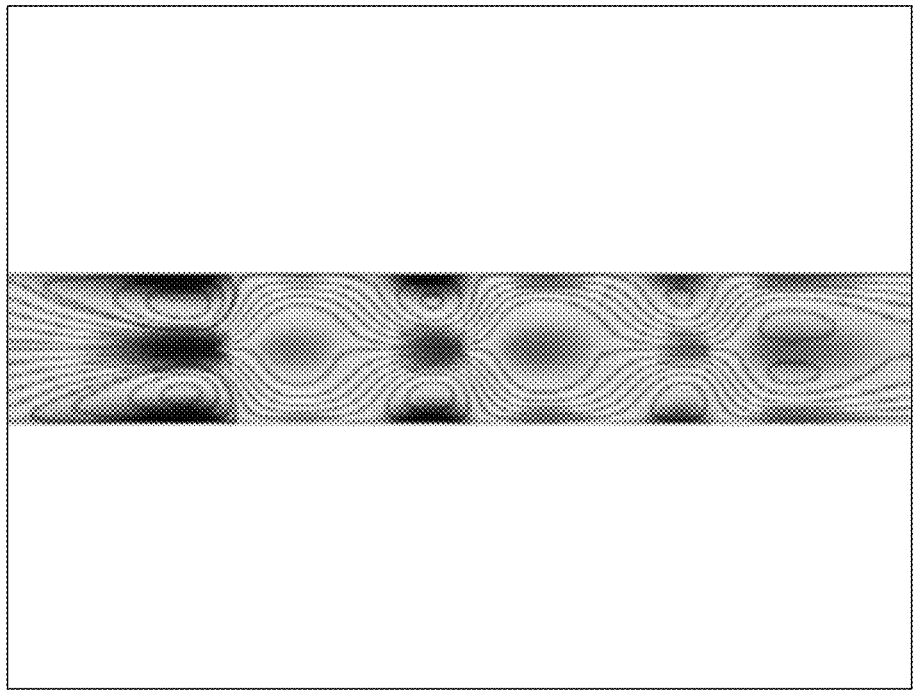
FIG. 10A shows streamlines over color-map of velocity of magnitude of a simulation of EHD-driven flows by PI Clack around 3 wire electrodes at −70 kV in a 2-D channel.
Figure 10B:
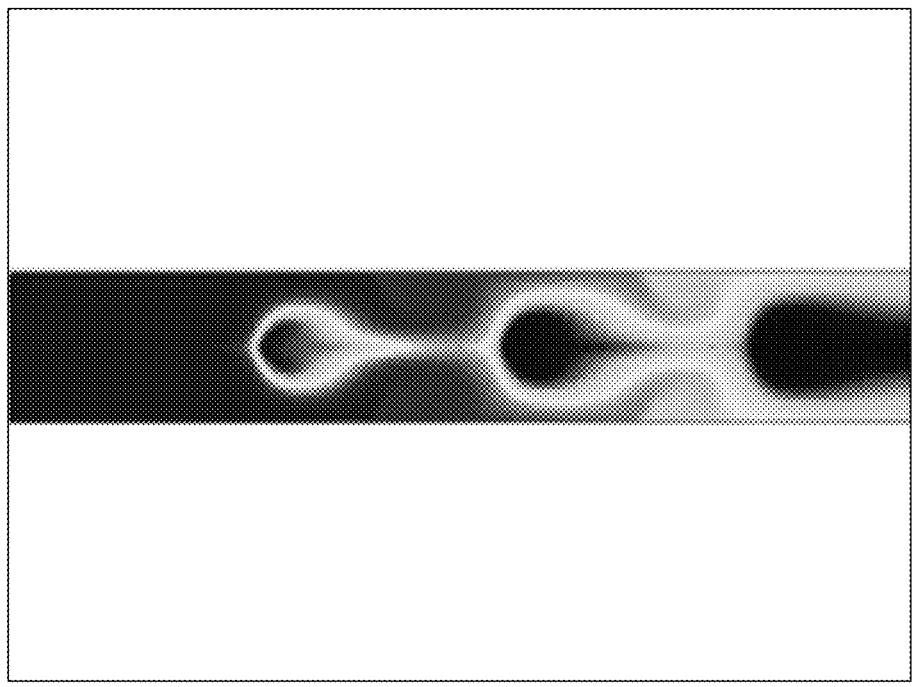
FIG. 10B is a concentration color-map showing pathogen inactivation due to RR attack, assuming simplified one-step kinetic mechanism; 67% inactivation efficiency.
Figure 10C:
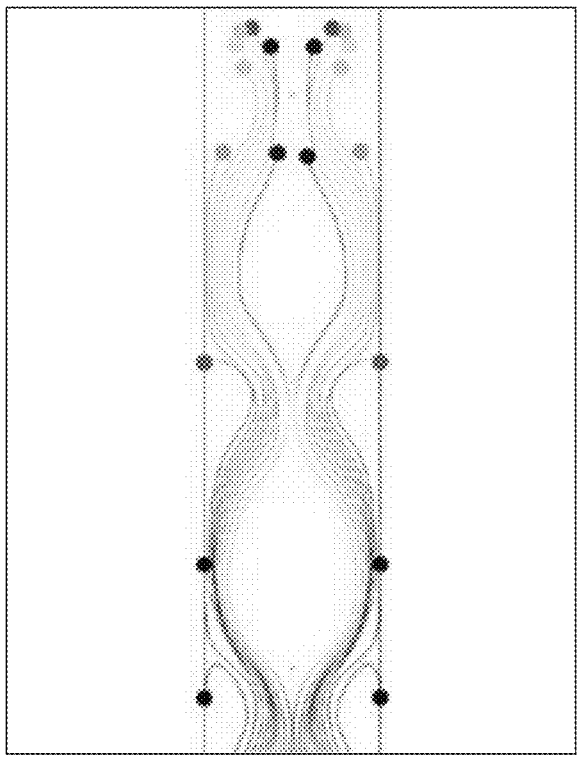
FIG. 10C shows trajectories of 1 μm aerosols with color-mapped RR dose, cumulative charge.
Figure 11:
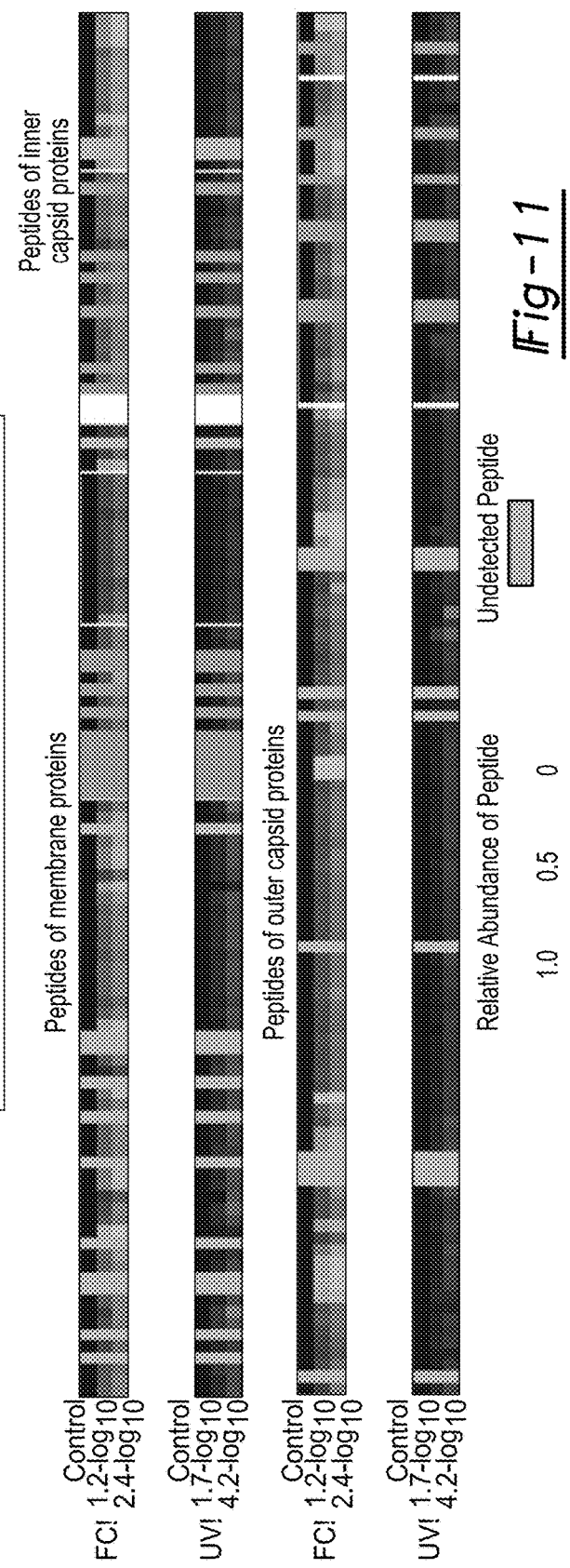
FIG. 11 shows reactions in φ6 virus proteome as virus is inactivated with free chlorine and UVC.

FIGS. 10A-10C presents numerical simulation results involving EHD phenomena. FIG. 10A-10C shows computed fluid streamlines overlaid on a color map of fluid velocity magnitude. Clearly evident is the strongly articulated, EHD-induced flow pattern highlighted by zones of flow convergence approaching each of the three wire electrodes along the centerline. The fluid dynamic vena contracta that occurs just upstream of each wire electrode focuses the fluid and its entrained sub-micron aerosols into the plasma stabilized above the wires' surfaces.

FIG. 10B shows numerical results for a simplified airborne pathogen inactivation process involving a one-step inactivation reaction (k=1000 m6/s-mol2) between suspended infectious aerosols and radially decaying concentrations of reactive species produced by the plasma at the wire electrodes' surfaces. The EHD enhancement nearly doubles the rate of inactivation in this simple simulation (67%) compared to a conventional channel flow with no such enhancement (34%). The nonuniform spatial distribution of reactive species also results in the suspended aerosols receiving nonuniform exposure to those species, leading to overall lower inactivation than would result from a more uniform exposure in e.g., a packed bed NTP. FIG. 10C explicitly shows this effect through numerical results predicting the accumulated charge and reactive radical (RR) dose (defined as the integral of RR concentration over particle trajectory) received by 20 1-micron aerosols in the same EHD channel flow. The 20 aerosols exhibit outcomes ranging from low RR dose received and rapid aerosol collection on the channel wall (dark, light blue) to high RR dose received for aerosols remaining in suspension (brown, orange). The lower RR dose received by aerosols farthest from the plasma may contribute to lower overall rates of inactivation, but may also present opportunities for other uses of NTPs in air based on recent work.

A recent study by Wang et al. demonstrated that NTP exposure can be used to formulate modified live vaccines from viruses. Their results showed that sub-lethal NTP exposure could render viruses non-infective while leaving intact the essential surface proteins whose presence stimulates a host immune response. The potential therefore exists for using NTPs to transform viable airborne viruses directly into modified live vaccines with particular applicability to military operations and bio-warfare/bio-terrorism countermeasures.

Figures 1A, 1B:
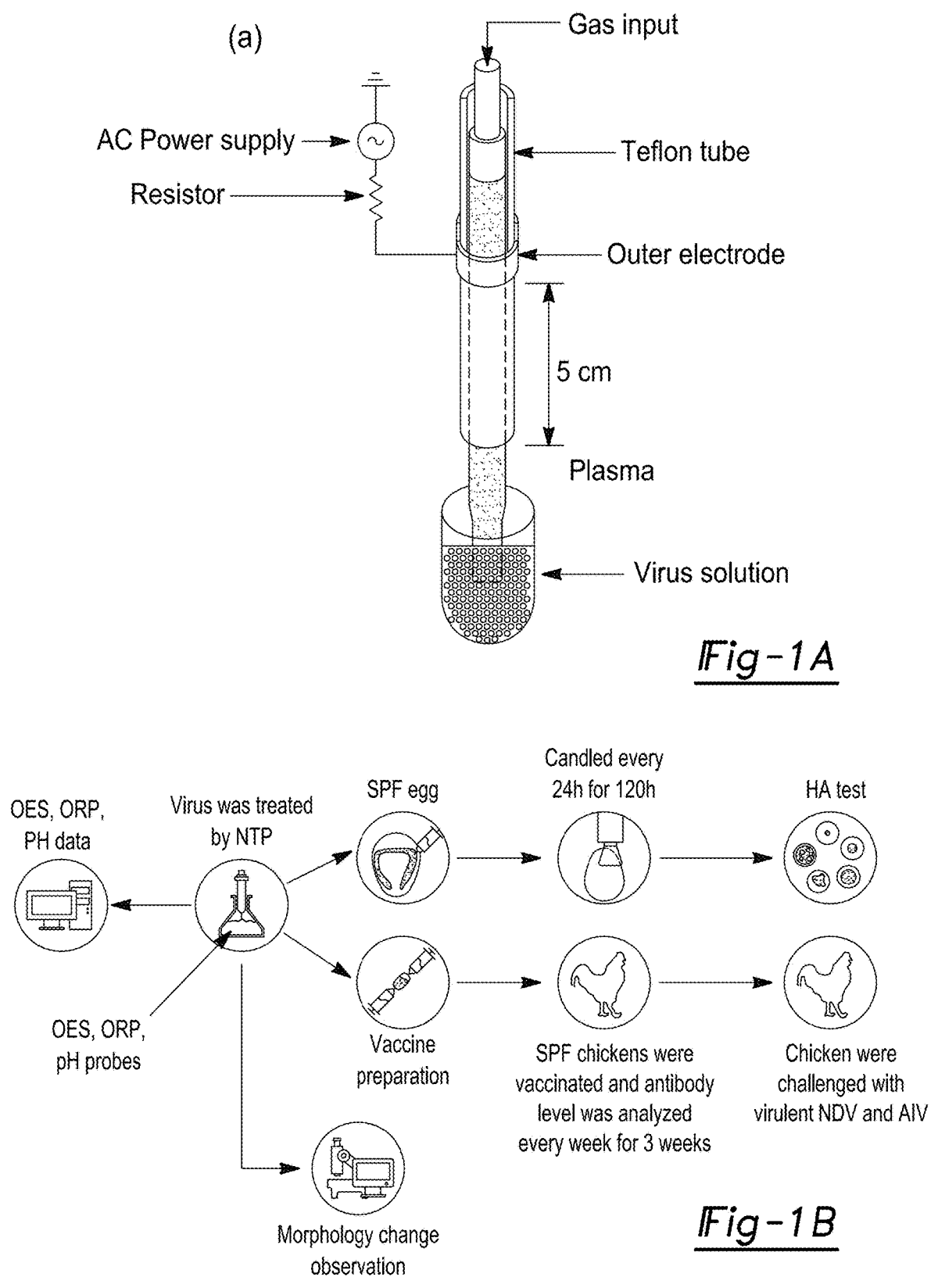

An NTP device is shown in FIG. 1A. The NTP jet was composed of a Teflon tube whose inner and outer diameters were 7 mm and 10 mm, respectively, and a high-potential electrode made of a copper foil with a thickness of 2 mm surrounded the Teflon tube 5 cm from the end of the tube. The plasma was generated by an 18 kV (peak-to-peak) sinusoidal alternating voltage source with a frequency of 10 kHz. The input current was set at ~2-2.5 A. A mixture of argon (Ar), oxygen (O2) and nitrogen (N2) containing 88% Ar, 2% O2 and 10% N2 at a flow rate of 5 L/min was used as the working gas. The plasma plume was approximately 5 cm from the end of the nozzle, with a temperature of 28° C.±3° C. The distance from the end of the nozzle to the virus allantoic fluid was 1 cm. The optical emission spectrum of the plasma from 200 to 850 nm was detected using a multi-channel fiber optic spectrometer (AvaSpec-2048-8-USB2, Avantes, Eerbeek, Netherlands) with a fiber optic cable placed along the nozzle axis with an end-on view. Representative species were assigned by referring to the database from the National Institute of Standards and Technology. The detailed geometry and operating parameters of the device are illustrated. The overall experimental procedure is shown in FIG. 1B.

NDV (LaSota strain) and AIV (H9N2, A/Chicken/Hebei/WD/98 strain) were propagated in 11-day-old SPF chicken embryos. The allantoic fluid was harvested, clarified by low-speed centrifugation and stored at −70° C. before use. To inactivate the virus by NTP, 10 mL of NDV-allantoic fluid was thawed at 37° C. and treated with NTP for different amounts of time (2 min, 4 min, and 6 min), and the same process was applied to 10 mL of AIV-allantoic fluid with NTP for 1 min, 2 min, 3 min and 4 min. Allantoic fluid containing NDV or AIV without NTP treatment was used as the control A conventional embryo lethality assay (ELA) and a hemagglutination (HA) test were performed to determine the viability of the viruses after NTP treatment. Subsequently, using Drakeol 6-VR as an oil adjuvant, inactivated oil-emulsified vaccines were prepared with NDV or AIV antigens treated by NTP and 0.1% formaldehyde. The SPF chicken embryos were supplied by Beijing Merial Vital laboratory Animal Technology Co., Ltd.

Viruses treated by different methods and the control sample were injected into 11-day-old SPF chicken embryos, with five embryos in each group. Based on previous studies 0-120 h was chosen as the monitoring time. The eggs were candled every 24 h, and the death number beyond 24 h was recorded until 120 h. Dead eggs were chilled at 4° C. Then, the ELA results were summarized.

The HA and HI assays were performed in accordance with OIE standard procedures. The HA titer was read as $\log_2$ of the highest dilution of antigen giving complete HA (no streaming). The HI titer was read as $\log_2$ of the reciprocal of the highest dilution of serum causing inhibition of HA. The samples with HA or HI titers of 4 $\log_2$ or higher were considered HA or HI positive.

A total of 165 28-day-old SPF chickens were tagged and divided randomly into 10 groups (saline, formaldehyde-NDV-vaccine, NTP-2 min-NDV-vaccine, NTP-4 min-NDV-vaccine, NTP-6 min-NDV-vaccine, form aldehyde-AIV-vaccine, NTP-1 min- AIV-vaccine, NTP-2 min-AIV-vaccine, NTP-3 min-AIV-vaccine and NTP-4 min-AIV-vaccine), with 30 chickens in the saline group and 15 chickens in each of the other groups. Each chicken in the vaccinated groups was inoculated subcutaneously with 0.2 mL of vaccine. Chicken sera were collected from the wing vein on day 0 (pre-vaccination) and on days 7, 14, and 21 (post-vaccination) and were tested for the presence of NDV-specific or AIV-specific antibodies using the HI test. The chickens were maintained in negative pressure isolators throughout the experiments.

The chickens were challenged according to a previous study, three weeks after vaccination, the chickens in the NDV groups were subcutaneously injected with 0.5 mL of 10 s embryo lethality dose (ELD50) velogenic NDV according to previous studies. Pictures were taken every 24 h, and the dead chickens were stored at 4° C. Clinical signs and deaths were monitored for 10 days post challenge. Sections of the trachea and glandular stomach were collected during necropsy and inspected. Chickens in AIV groups were injected with 0.5 mL of 10 s ELD50 virulent AIV. Cloacal swabs and throat swabs were collected into PBS, centrifuged and filtered before injection into 11-day-old chicken embryos for HA testing. Ten days later, all live birds were killed by intravenous pentobarbital sodium (Merck, Germany) overdose.

ORP and pH assessment of allantoic Ifuid containing NDV during NTP treatment was carried out using an ORP probe following the operation procedure in previous studies. ORP and pH values were read every 60 s for a total of 10 min. The experiment was randomly performed three times.

To further explore whether changes in the pH or ORP play a dominant inactivation role, the viral allantoic fluid containing antioxidant (Vc, 2M) was treated by NTP and injected into SPF chicken embryos. ELA was carried out to test whether the virus was protected from inactivation, and pH tests were carried out during the treatment process.

Scanning electron microscopy (SEM) was employed to study the overall morphological changes of viruses treated by NTP for different durations. The viral allantoic fluid was centrifuged at 100,000×g and fixed with 2.5% glutaraldehyde overnight at 4 C before being dehydrated through a graded ethanol series (30-100% ethanol) at room temperature. Finally, the viruses were dried, and then SEM was used to study the overall morphological change of the viruses. Because we were limited by the magnification of SEM, we employed transmission electron microscopy (TEM) to study the detailed changes of a single virus (×50,000). After different treatment times, the viral samples for TEM were prepared. Then, TEM was used to observe the detailed changes of a single virus.

Student's t-test was used to compare the antigen titer and the antibody titer between NTP groups and the corresponding formaldehyde groups. There are significant differences when the p-value is <0.05.

Figure 2A:
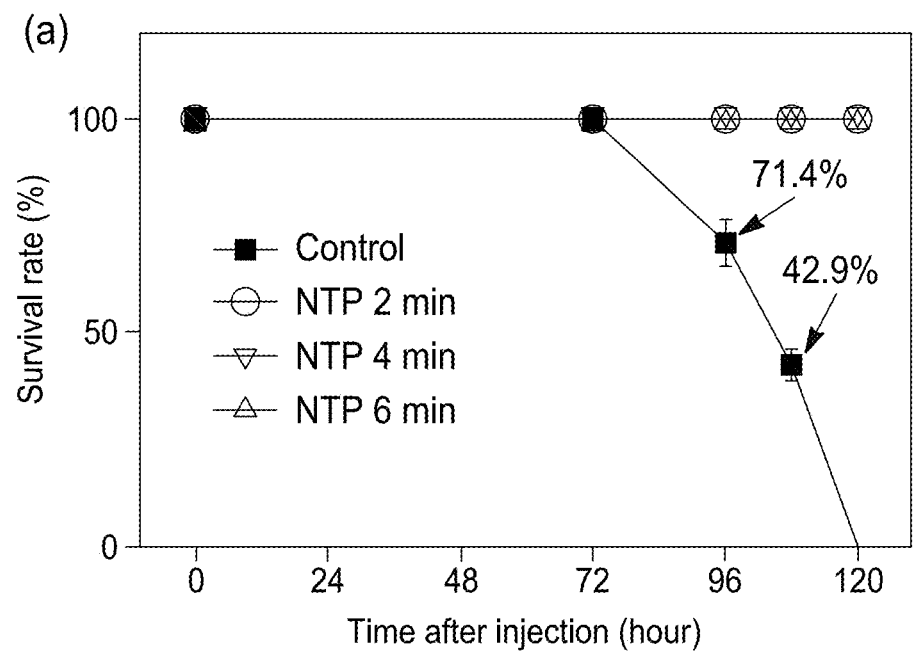
FIG. 2A shows inactivation confirmation of the viruses the survival rate curve of embryos at 120 h post injection of NTP-treated and non-treated NDV antigens.
Figure 2B:
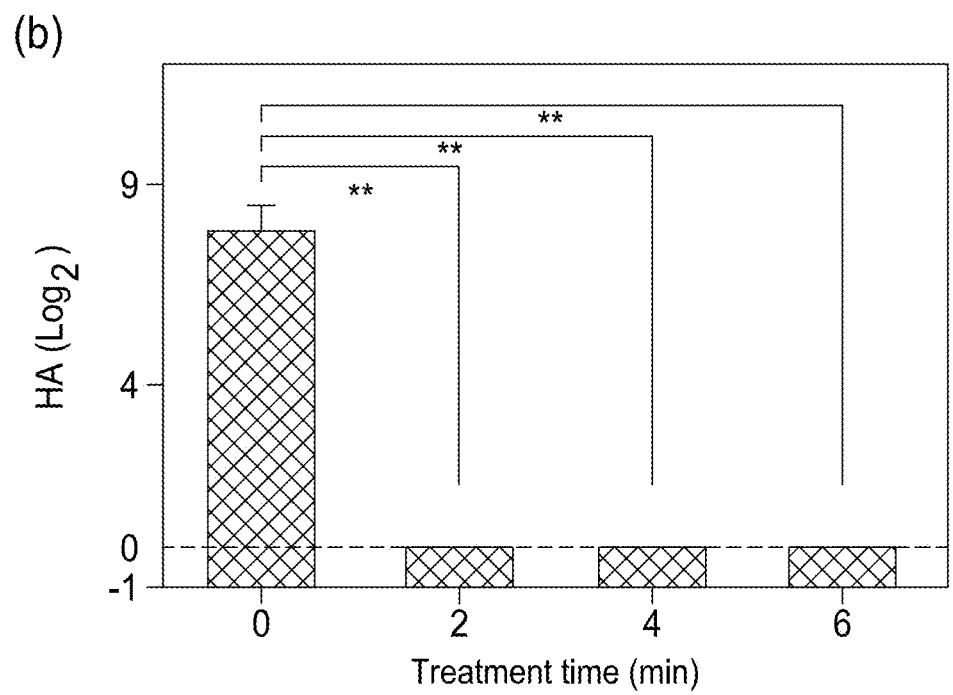
FIG. 2B shows the HA titers of allantoic fluid collected from embryos injected with NTP-treated and non-treated NDV antigens.
Figure 2C:
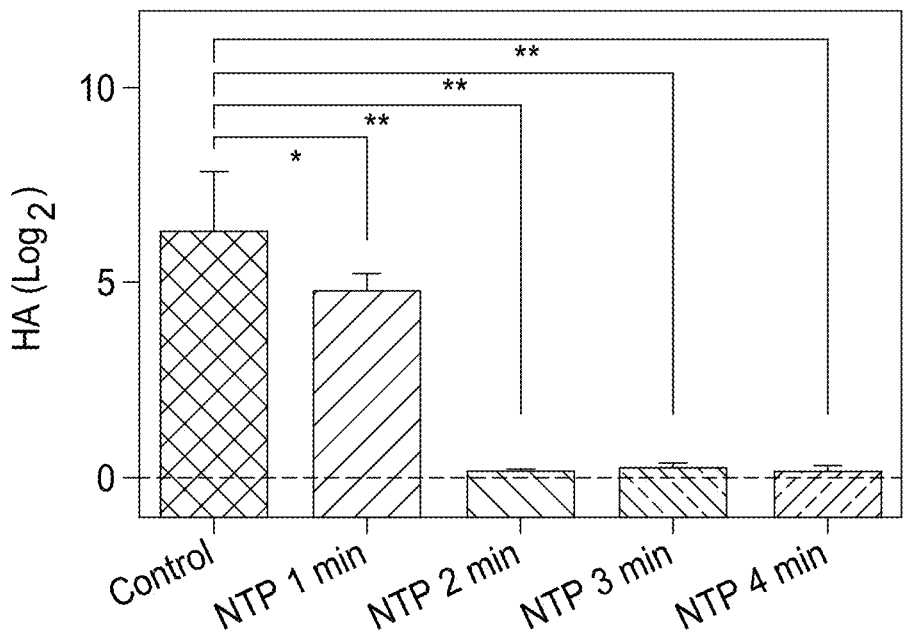
FIG. 2C shows the HA titers of allantoic fluid collected from embryos injected with NTP-treated and non-treated AIV antigens.

As illustrated above, the first step is to ensure that the virus is inactivated by NTP. The ELA results of NDV are shown in FIG. 2A. The survival rates of chicken embryos that were injected with non-NTP-treated LaSota NDV were 71.4%±5.1% at 96 h and 42.9%±3.0% at 108 h, and all chicken embryos were killed in 120 h with an average HA titer of 7.86±0.46 $\log_2$ (FIG. 2B). However, embryos injected with NTP-treated (2 min, 4 min and 6 min) NDV all survived, but no HA titer was detected (FIGS. 2A and 2B). The HA test results of NTP-treated AIV are shown in FIG. 2C. Although the embryos injected with AIV in each group, both non-NTP and NTP-treated, survived after 120 h, the HA test results showed that an NTP treatment time of over 2 min could lead to negative HA results, and the HA values of the NTP-1 min-AIV and control groups were 4.75±0.43 $\log_2$, respectively.

Figure 3A:
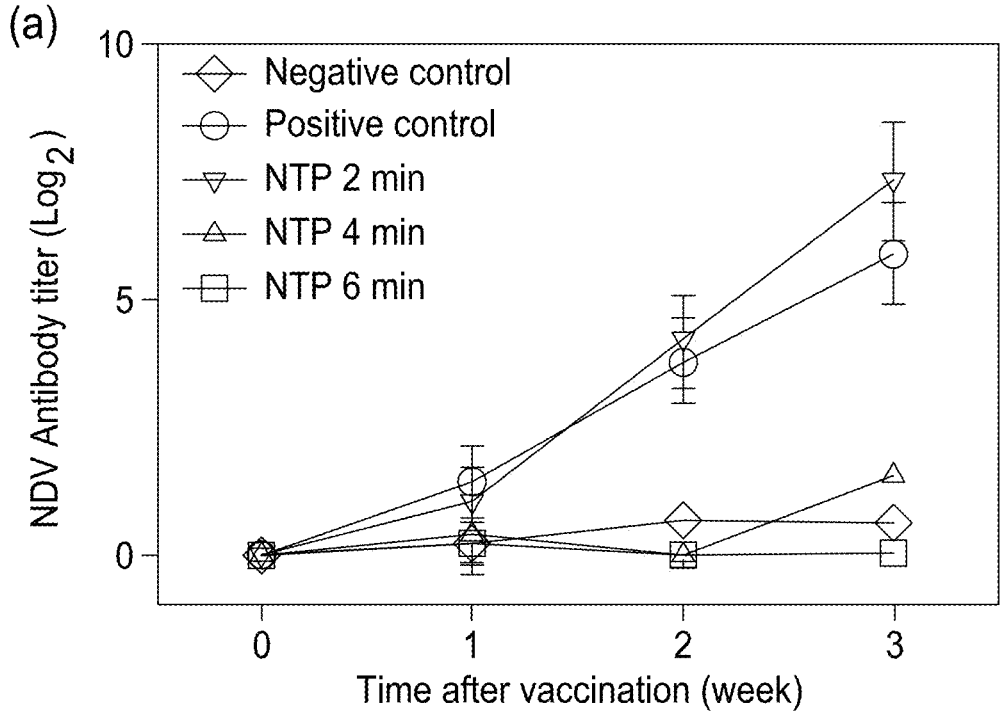
FIG. 3A shows antibody titers of serum collected from vaccinated with NDV-specific antibody titers.
Figure 3B:
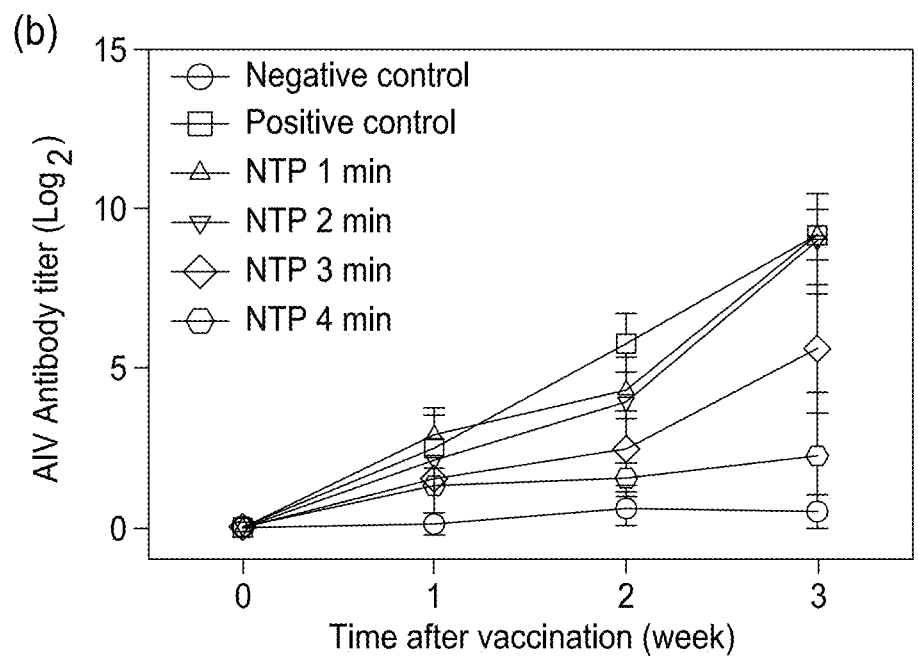
FIG. 3B shows antibody titers of serum collected from vaccinated chickens with AIV-specific antibody titers.

Vaccines in the NTP groups and the formaldehyde groups were well absorbed by vaccinated chickens without obvious swelling at the injection site. Antibody titers against the NDV vaccine are shown in FIG. 3A. In the NTP-2 min-NDV-vaccine group and the formaldehyde-NDV-vaccine group, the antibodies emerged 7 days post vaccination, and their levels increased sharply during the following 2 weeks. Three weeks after vaccination, chickens vaccinated with NTP-2 min-NDV-vaccine showed higher titers (7.3±1.2) than chickens vaccinated with formaldehyde-NDV-vaccine (5.9±1.0) (p<0.05). The NDV-specific antibody levels of the groups vaccinated with NTP-4 min-NDV-vaccine and NTP-6 min-NDV-vaccine were as low as that of the unvaccinated group (p>0.05) (FIG. 3A). Antibody titers for the AIV vaccine are shown in FIG. 3B. Chickens vaccinated with NTP-1 min-AIV-vaccine and NTP-2 min-AIV-vaccine showed a similarly increased titer when compared with chickens in the formaldehyde-AIV-vaccine group, emerging on day 7 and increasing significantly to ~9 log 2 in the following two weeks. Comparably, AIV antibody titers in chickens injected with NTP-3 min-AIV-vaccine were detected on day 7 post vaccination and reached 5.6±2.0 log2 at 2 weeks, while chickens in the NTP-4 min-AIV-vaccine group and the unvaccinated group showed a negative HI test (2.3±1.9 $\log_2$, respectively).

Figure 4A:
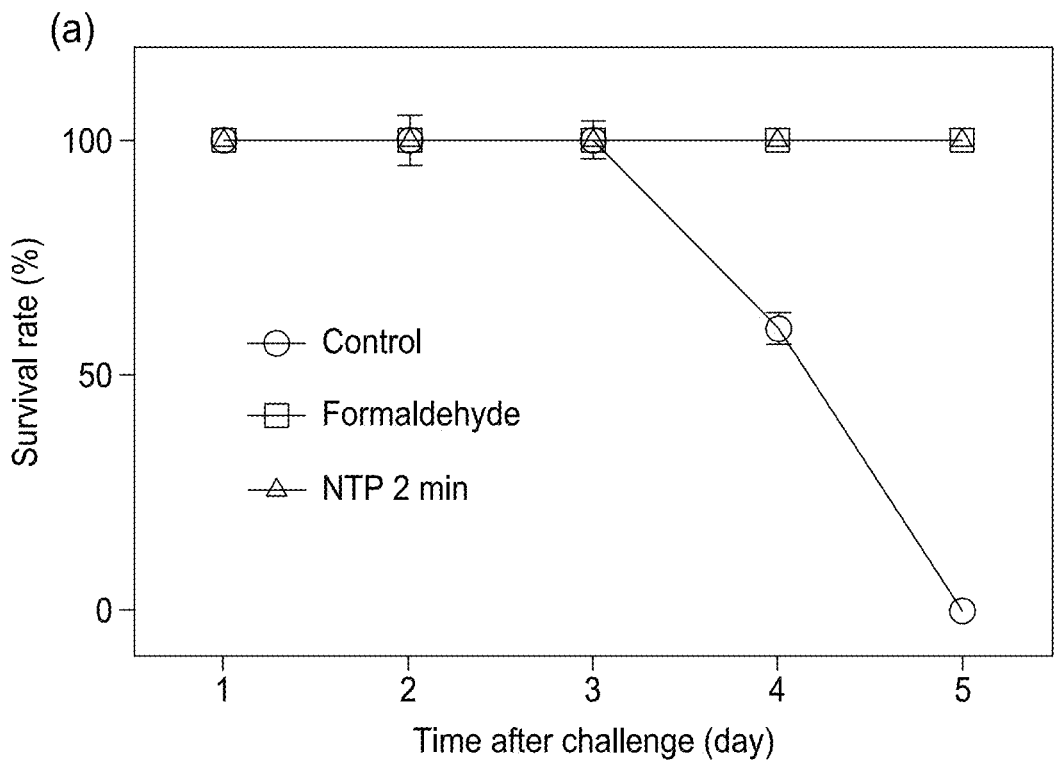
FIG. 4A shows the survival rates of chickens against a challenge NDV study.

The results of the NDV challenge test are shown in FIGS. 4A and 4B. For NDV groups, all chickens vaccinated with NTP-2 min-NDV-vaccine and formaldehyde-vaccine survived, whereas all non-vaccinated chicken died within 4 days, with severe signs since the third day (FIG. 4A). Before death, they showed clinical signs and postmortem lesions typical of ND, including depression (14 of 15), conjunctivitis (13 of 15), dyspnea (10 of 15) and diarrhea (14 of 15). Hemorrhage throughout the gastrointestinal and proventriculus (13 of 15) was detected at necropsy (FIG. 4B). For the AIV vaccine groups, however, no significant clinical signs were observed in each group. Overall, 60%±5.7% of embryos that were injected with swab samples in the saline group and 10%±4.5% of embryos in the NTP-1 min-AIV-vaccine group were HA positive, wheras the embryos in the NTP-2 min-AIV-vaccine, NTP-3 min-AIV-vaccine, NTP-4 min-AIV-vaccine and formaldehyde groups were HA negative.

Figures 5A, 5B:
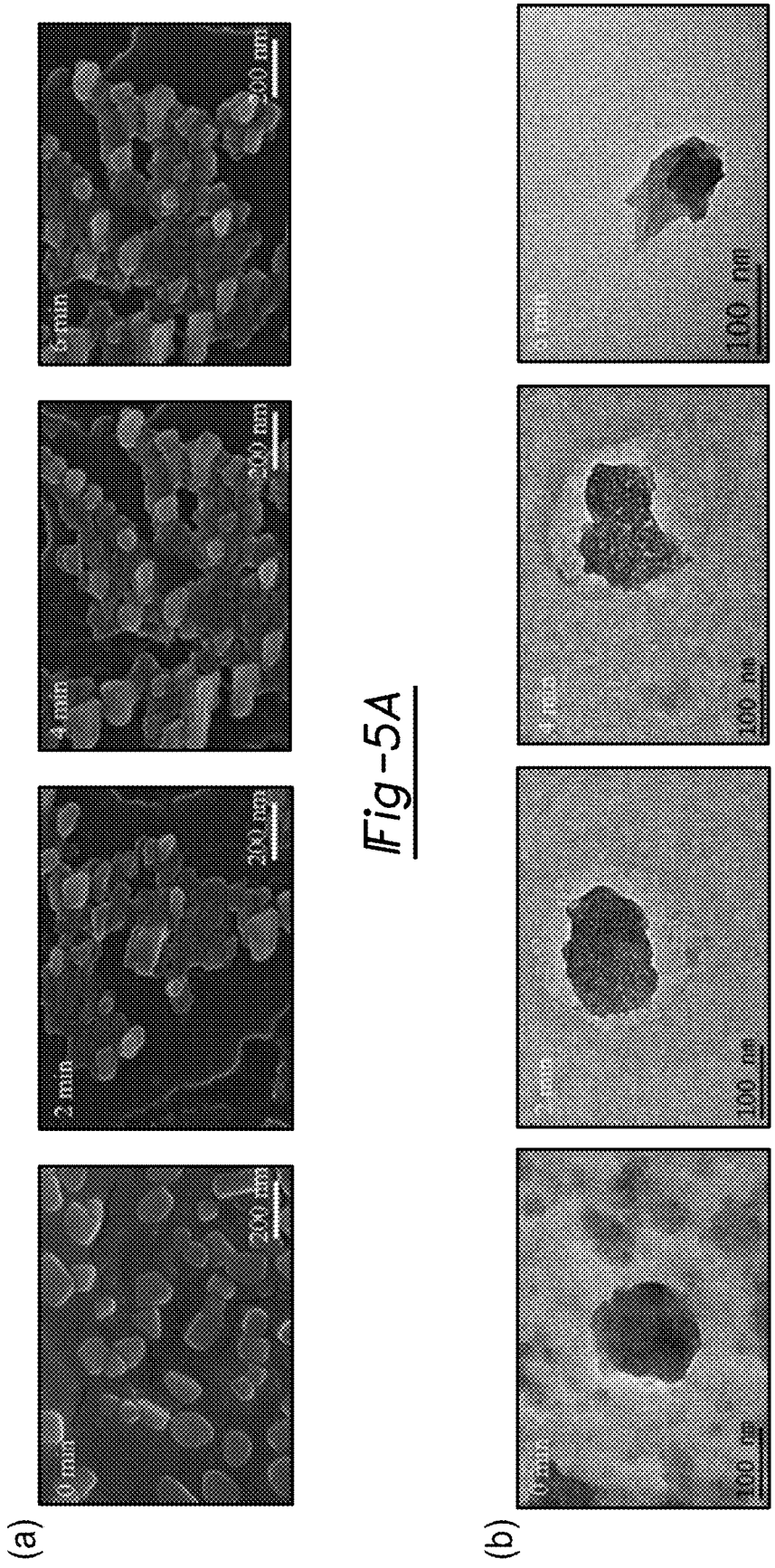
FIG. 5A shows typical SEM images of NDV before and after NTP treatment.
FIG. 5B shows typical TEM images of NDV before and after NTP treatment.

Morphological changes brought about by NTP treatment are valuable for explaining the mechanism of the technology. We employed SEM and TEM to study the overall surface changes of NDV treated for different amounts of time. Typical images of NDV treated for different times are shown in FIGS. 5A and 5B. It was observed that after 2 min of NTP treatment, the viral structure was damaged and the morphology was abnormal. Additionally, only a few viruses on the top surface maintained their original morphology (FIG. 5A). Prolonged treatment times led to more serious morphological changes, as observed by TEM (FIG. 5B). The original shape of NDV was rounded, and after 2 min of NTP treatment, slight shrinking was observed. The viral morphology was remarkably destroyed when the treatment time was further prolonged from 4 min to 6 min.

Figure 6A:
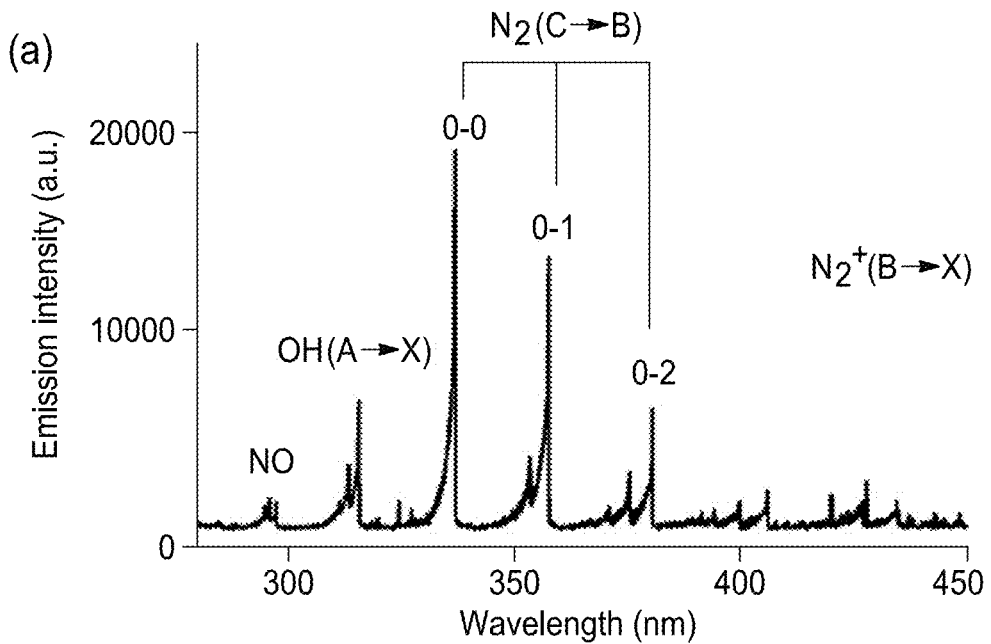
FIG. 6A shows the results from 250 to 450 mm of an optical emission spectrum of $Ar/O_2/N_2$ (2%) NTP at a gas flow rate of 5 standard liters per minute and an input current of 2.5 A.
Figure 6B:
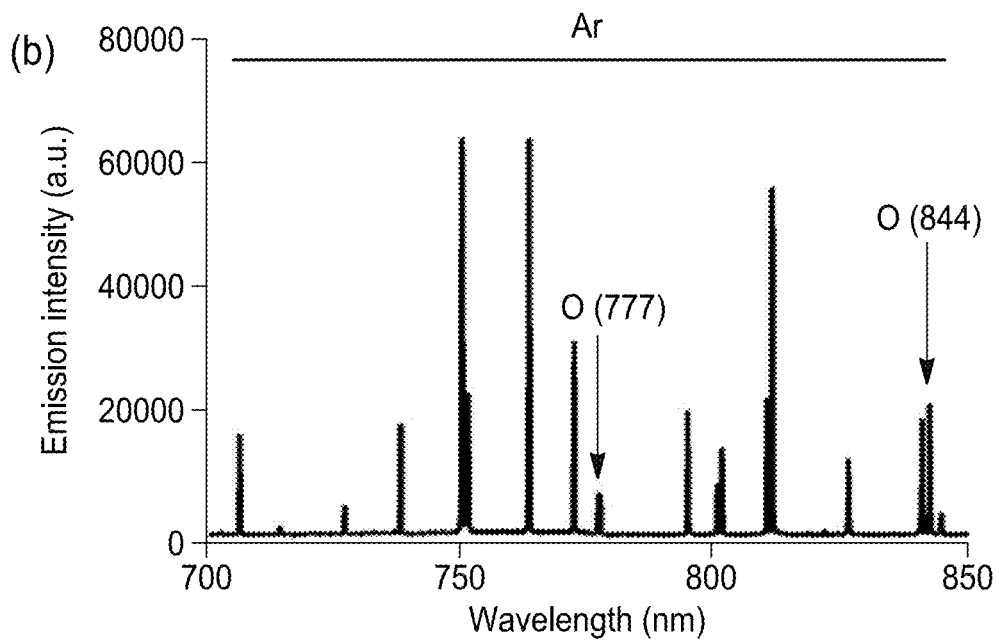
FIG. 6B shows the results from 700 to 850 mm of an optical emission spectrum of $Ar/O_2/N_2$ (2%) NTP at a gas flow rate of 5 standard liters per minute and an input current of 2.5 A.
Figure 6C:
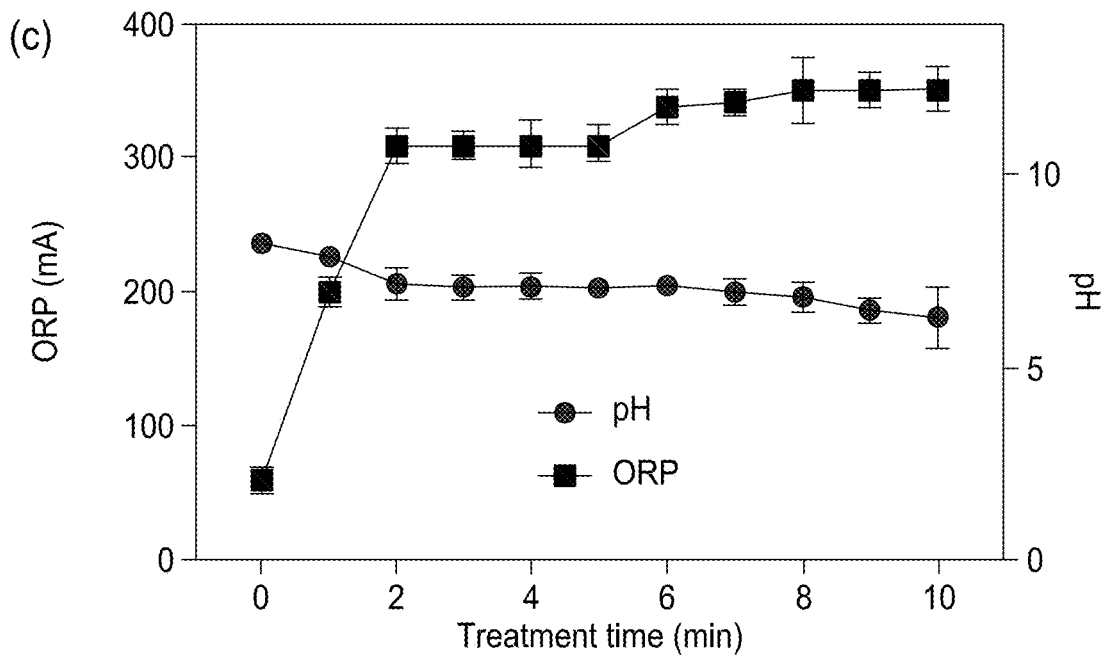
FIG. 6C shows the results from real time detection of ORP and pH test of NDV allantoic fluid treated by NTP for 10 min.

As shown in FIGS. 6A and 6B, NTP optical emissions from 250 nm to 450 nm and from 700 nm to 850 nm are analyzed. Ar and atomic 0 emissions at 111 and 844 nm, NO emission at 290 nm, N2 emission at 337 nm, and the —OH radical at 310 nm dominate the spectrum. In addition, the oxidative and acid properties of allantoic fluid containing NDV during NTP treatment are plotted in FIG. 6(c). The results show that the ORP increases linearly during the NTP treatment time of 10 min. The initial ORP of virus allantoic fluid was ~50 mV, while it increased to 300 mV in 2 min. A AORP of 250 mV indicates a remarkable antioxidant capacity increase in the virus allantoic fluid. Additionally, in our study, the pH of the virus allantoic fluid decreased slightly from ~8.5 to ~6.5 (FIG. 6C).

Allantoic fluid containing NDV and antioxidant (Vc, 2 M) was injected into embryos before they were treated with NTP. The ELA results showed that embryos injected with Vc all died in 120 h (Supplementary Table 1). Interestingly, the pH value of allantoic fluid was still ~6.5. This phenomenon suggests that oxidation is more important than low pH during the NTP inactivation process.

The fact that infectious diseases among poultry can result in great economic and health losses to humans emphasizes the importance of vaccines, Currently, inactivated vaccines are still one of the most widely used vaccine techniques in poultry for preventing infectious diseases, However, the deleterious effects of traditional inactivating agents such as formaldehyde and (3-propiolactone indicate that a safer and more effective method is necessary for producing inactivated vaccines. Based on the previous study of NTP inactivation of pathogens, we focused on the potential application of NTP toward inactivated vaccine preparation in this study. As Newcastle disease and Avian influenza are two of the common diseases that can not only infect a large variety of animal species but also cause 100% flock mortality, the feasibility of NTP as an alternative method for the preparation of inactivated vaccines against these two diseases was investigated.

In consideration of the safety of vaccines, the first step is to confirm the inactivation of the viruses by NTP. The ELA results showed that neither NTP-treated NDV nor NTP-treated AIV could cause death to SPF embryos in 120 h. Moreover, the HA assay of allantoic fluid extracted from the embryos showed that after NTP treatment for over 2 min, NDV lost its ability to proliferate. After treatment with NTP for 1 min, the AIV virus maintained its viability. However, a treatment time of 2 min or more could induce complete inactivation of AIV viruses. This suggests that NTP has a dose effect during the inactivation process. Afterwards, two types of oil vaccines were prepared using antigens treated by NTP. Viruses inactivated by 0.1% formaldehyde were employed as positive control groups in this study. Chickens vaccinated with NTP-2 min-NDV-vaccine showed a similar antibody titer curve and exhibited a higher NDV titer 3 weeks post vaccination when compared with the formaldehyde-NDV-vaccine group. Nevertheless, it is worth mentioning that an excessive NTP treatment will lead to a significantly lower NDV antibody titer, which is comparable to the negative control group. Similarly, NTP-2 min-AIV-vaccine can induce a similar AIV antibody titer compared to its positive control group, while an overdose NTP treatment can lead to a decrease in the AIV antibody titer FIG. 3B. These results suggest that there is a specific NTP treatment time for preparation of both vaccines, and overdose NTP treatment probably leads to the destruction of the antigenic determinant of the virus, causing the vaccine to no longer induce antibody production. Moreover, results of challenge tests suggest that NDV-specific antibody titers induced by NTP-2 min NDV vaccine and AIV-specific antibody titers induced by NTP-2 min AIV vaccine can effectively protect chickens from infection by vel- ogenic NDV and velogenic AIV, respectively, demonstrating the feasibility of NTP as an alternative method to produce inactivated NDV and inactivated AIV vaccines.

Considering the similarity of NDV and ADV, we chose NDV to further explain the possible underlying mechanism of why NTP, at an appropriate dose, can inactivate the virus with its antigenic determinant remaining. The ORP value can comprehensively represent the redox potential level of the system. Previous studies indicated that oxidation was probably the key factor in the NTP inactivation process. Oxidative agents and low pH were both indicated to have antiviral effects. In this study, the pH decreased slightly during the treatment process. Additionally, the ΔORP incrased by 250 mV, suggesting a remarkable increase in the antioxidant capacity of the virus allantoic fluid. However, the results that an antioxidant (Vc, 2 M) can protect the virus from inactivation while the pH still decreased to approximately 6.5 in this study (FIGS. 6A-6C) indicate that oxidation, not low pH, plays a more important role during the inactivation process by NTP. We also analyzed the main components of NTP by OES analysis. Reactive nitrogen species (RNS) such as NO, $N_2$, (C-B) and reactive oxygen species (ROS) such as —OH and O were detected (FIG. 6). Using an electron spin resonance (ESR) test, a significant amount of $O_2$ was detected in our previous study. We speculate that a series of chemical reactions among ROS and RNS occur in the virus allantoic fluid system. RNS and ROS in the system lead to a significant increase in the ORP, which results in inactivation of the virus.

The strong oxidation characteristic of NTP overdose resulted in distinct morphological changes in the virus, which further decreased the virulence of the virus and destroyed the antigenic determinant. The results of this study suggest that although morphology damage was one of the main causes of NDV inactivation, NTP in an appropriately timed NTP dose could effectively inactivate the virus without severely affecting the antigenic determinant. We conjecture that if an overdose of NTP is administered, it is hard for the virus to retain the integrity of its antigenic determinant, which results in the loss of immunogenicity. These results can explain why NDV treated with NTP for 2 min can be prepared as a vaccine and can induce enough antibodies to prevent the invasion of velogenic NDV, while NTP treatment for over 4 min could destroy the NDV morphology and lead to the loss of immunogenicity. Moreover, this theory can reasonably explain why NTP-3 min-AIV-vaccine and NTP-4 min-AIV-vaccine induced lower antibody titers than NTP-2 min-AIV-vaccine.

In summary, NTP was introduced to treat the NDV and AIV allantoic fluids for preparation of inactivated-NDV-vaccine and inactivated-AIV-vaccine. The results of SPF chicken experiments suggest that it is feasible for NTP, with an appropriate treatment time, to produce inactivated AIV and NDV vaccines and to induce similar or higher specific titers of antibody compared with the conventional formaldehyde inactivation method. ROS and RNS are believed to play a significant role during the inactivation process. As an alternative strategy, the plasma technology could open a gateway to vaccine preparation in stockbreeding.

In a separate study, four model viruses are considered (FIG. 18). These viruses were selected based on their varied physical characteristics (e.g., enveloped vs nonenveloped, particle size, and genome type) and due to their ability to be readily propagated to high titers. The last point is critical for studying the reaction chemistry in the virus particles. The protein and lipid mass spectrometry analyses require proteins and lipids concentrations that are not possible when the experiments are conducted with virus concentration less than than ~$10^{10}$ IU/mL. ϕ6 is propagated in its bacterial host *Pseudomonas syringae* pv. phaseolicola grown in Luria-Bertani (LB) medium containing 5 g $L^{-1}$ NaCl at 26° C. To propagate ϕ6 stocks, soft LB-agar (0.7% agar) layers are removed from the double-layer plates, and dissolved in 3 mL of LB medium. MS2 is propagated in its *Escherichia coli* hosts ATCC 15597. The nonenveloped virus is purified with an Econo Fast Protein Liquid Chromatography system (Bio-Rad) equipped with a HiPrep Sephacryl S-400 HR column (GE). The collected viral fraction is concentrated with 100 kDa Amicon ultracentrifugal filters (Millipore), and filtered through a 0.22 μm PES membrane filter. VSV Indiana Strain is propagated with BHK-21 cells in high-glucose Dulbecco's modified Eagle medium (DMEM). Phi6, *P. syringae* is grown in Luria-Bertani (LB) medium containing 5 $g^{L-1}$ NaCl. Cells and debris will be removed from the virus suspensions by filtering it through 0.22 μm polyethersulfone membranes. The filtered enveloped virus suspensions are concentrated in a lab-scale tangential flow filtration system (Millipore) outfitted with a 30 kDa cellulous filter and then purified in step sucrose gradients. Virus purity, which is important for controlled oxidant exposure, will be confirmed by SDS-PAGE with 8-16% TGX™ precast protein gels (Bio-Rad), according to the manufacturer's instructions. The final virus stocks will be filter-sterilized with 0.22 μm PES membranes, aliquoted, and stored at −80° C. until use.

Viral aerosols suspended in air is the result of evaporating fine mists of ~1 μm droplets generated from bulk PBS solutions by an ultrasonic atomizer. Ultrasonic atomizers produce more uniformly sized droplets than other methods, droplets that evaporate more consistently and completely. We have previously demonstrated an existing non-thermal plasma (NTP) reactor (FIG. 19) whose operating conditions and experimental protocols have been established and which provides the environment for systematically exposing viral aerosols to oxidizing environments. NTPs are stable electrical discharges that produce radicals and excited species such OH—, O., and OH. in air that quickly react to form more stable $O_3$ and $NO/NO_2$. Viral aerosols are exposed to three oxidizing environments: 1) radicals and excited species within the NTP, 2) $O_3$ and $NO/NO_2$ in air downstream of the NTP, and 3) $O_3$ $NO/NO_2$ and trace ROC (limonene) in air downstream of the NTP, representative of air pollutant compositions associated with OAF. FIG. 20 details the conditions of oxidant exposure to be established in the NTP reactor. Proposed concentrations of $O_3$, $NO/NO_2$, and ROC are comparable to those measured in previous studies of airborne pathogen inactivation and OAF; ROC are concentrations will be directly controlled based on the flow rates of air and (liquid) limonene. $O_3$, $NO/NO_2$ concentrations will be controlled based on air flow rate and NTP applied voltage and power, with the option of installing an activated carbon $O_3$ filter at the NTP reactor outlet to impose $O_3$ concentrations lower than those produced at the minimum voltage for the onset of electrical breakdown. The NTP reactor (FIG. 20) is a packed bed of 500 ¼" borosilicate beads sandwiched between electrically energized (12-30 kV AC, 60 Hz) brass mesh electrodes. Twin liquid impingers continuously extract (1 slpm) and collect viral aerosols in 20 ml dilution buffer at locations before and after oxidant exposure. We have demonstrated that further oxidation of viruses in the impingers by absorbed $O_3$ or $NO/NO_2$ is effectively quenched by the addition of sodium sulfite, a capability that favors liquid impingers over gel-based biosamplers for collecting viruses. A 3.4 m segmented quartz extension to the reactor is proposed to allow longer exposure times of the viral aerosols to the weaker oxidants $O_3$ and $NO/NO_2$.

Direct measurements of radical and excited species concentrations are not possible in this configuration, but are needed to establish dose-response relationships and infer kinetic parameters of inactivation. Concentrations of such short-lived species will be determined from numerical simulations of plasma activated reactions using a comprehensive reaction mechanism for humid air plasma chemistry, calculated based on the operating conditions of the NTP reactor, and validated against its measured $O_3$ and $NO/NO_2$ downstream. Kushner has developed global and multidimensional models of dielectric barrier discharge (DBD) and atmospheric pressure plasma jets (APPJs) in the context of plasma biotechnology and pollution abatement. The humid air plasma model for repetitively pulsed DBDs, directly applicable to this reactor, has 79 gas phase species and 1,680 gas phase reactions. FIG. 4 shows sample results for the reactive oxygen species (ROS) and reactive nitrogen species (RNS) for the first and 5000th pulse of a DBD sustained in humid air at a repetition of 500 Hz. These results were produced using the global plasma model Global_Kin developed by Kushner.

Concurrent with the virus inactivation kinetic studies, the chemical reactions that take place in the virus particles as they are exposed to oxidants and UV radiation will be characterized. Samples that are captured following exposure to oxidants and radiation are tittered to assess the extent of virus inactivation. The samples are then split into three, and analyzed separately for reactions in their proteins, lipids, and nucleic acids.

Protein reactions are analyzed with quantitative mass spectrometry techniques. Following exposure to UV and oxidants, virus samples are combined with equal amounts of $^{18}$O-labeled internal standards and the mixture are digested with trypsin or chymotrypsin at 37° C. overnight. The digests are then analyzed by mass spectrometry. Specifically, 20 μL aliquots of the virus protein digests are loaded on an Accucore aQ column (50×2.1 mm, 2.6 μm particle size, ThermoFisher Scientific) attached to a Accucore aQ Defender guard column (ThermoFisher Scientific). Full mass spectrometry (MS) scans and data-dependent tandem mass spectrometry (dd-MS2) scans are conducted with a Q Exactive Orbitrap high resolution mass spectrometer (ThermoFisher Scientific) in positive ion mode (Table S2). Raw mass spectrometric results are searched against customized protein databases with Mascot Distiller (2.6.2.0) on a local Mascot server.

Lipids are extracted following methyl-tert-butyl ether (MTBE) protocol. Lipid extracts (20 μL) are injected on an Accucore aQ column (50×2.1 mm, 2.6 μm particle size) attached to a Accucore aQ Defender guard column at a flow rate of 200 μL $min^{-1}$. Full MS and dd-$MS^2$ scans are operated in negative ion mode conducted with aQ Exactive Orbitrap high resolution mass spectrometer. Lipids are identified with LipidXplorer software and peak areas are measured with TraceFinder 3.2 (ThermoFisher Scientific). The relative abundances of virus lipids ($L/L_0$) are calculated based on established the calibration curves.

The viral genomes are extracted by QIAamp viral RNA mini kits (Qiagen). Several primer sets for the virus genomes are designed to cover at least 25% of the genome sequences. RT-qPCR reactions are conducted in a Mastercycler ep RealPlex 2 system (Eppendorf) with Gotaq OneStep RT-qPCR kits (Promega). Standards used for the RT-qPCR calibration curves are obtained from Integrated DNA Technology (IDT). The reaction kinetics of RT-qPCR amplicons are likely to be modeled with first-order kinetics, and the extent of the entire genome reaction predicted by extrapolating RT-qPCR results from the region covered by RT-qPCR to the entire genome.

$$\ln\left(\frac{N_i}{N_0}\right) = -k_{g,i}D$$

$$\log_{10}\left(\frac{N}{N_0}\right) = \left(\frac{\sum_i L_i}{\sum_i L_{amp,i}}\right)\sum_i \log_{10}\left(\frac{N_i}{N_{0,i}}\right)$$

Where, $N_i$ is the concentration of RT-qPCR amplicon I (gc $mL^{-1}$), $N_{0,I}$ is the mean concentration of RT-qPCR amplicon I in controls (gc $mL^{-1}$), $k_{g,I}$ is the first order decay rate constant of RT-qPCR amplicon I (L $mg^{-1}$ $s^{-1}$ or $cm^2$ $mJ^{-1}$), $\log_{10}$ ($N/N_0$) is the $\log_{10}$ decay of the entire virus genome; $L_i$ is the size of genome I (b or bp); $L_{amp,i}$ is the size of amplicon I (b or bp).

Studies of airborne pathogen inactivation kinetics can be conducted in a similar fashion to chemical kinetic flow reactor studies where the sampling of reactants and products in a flow is discretized in space, and thus by virtue of the flow velocity, also in time. Analogous studies with bacteria are used to develop, e.g., Chick-Watson or modified Chick-Watson disinfection kinetic models of the temporal evolution of the viable or infective fraction of the original pathogen population, ln(N/N0)=−kCT. Few studies have explored NTP inactivation of airborne pathogens. Fridman and co-workers studied inactivation of airborne bacteria using NTPs, however their closed-loop apparatus recirculated the air stream leading to accumulation of residual $O_3$ and NOx in each trial, confounding the effects of direct plasma exposure and oxidation by $O_3$ and $NO_x$. In using a single dense grid of cylindrical electrodes, their calculations of direct plasma exposure time for the suspended bacteria fail to consider EHD effects such as those in FIGS. 10A-10C. Wu et al. most recently reported aerosolized MS2 inactivation rates while varying carrier gas and applied power within a wire-cylinder NTP configuration. However, the results do not mention what fraction of the charged aerosol was collected electrostatically within the apparatus. Since such collection would lower apparent post-treatment pfu counts, there could be a positive bias in the calculated inactivation efficiency.

Figures 12A, 12B, 13:
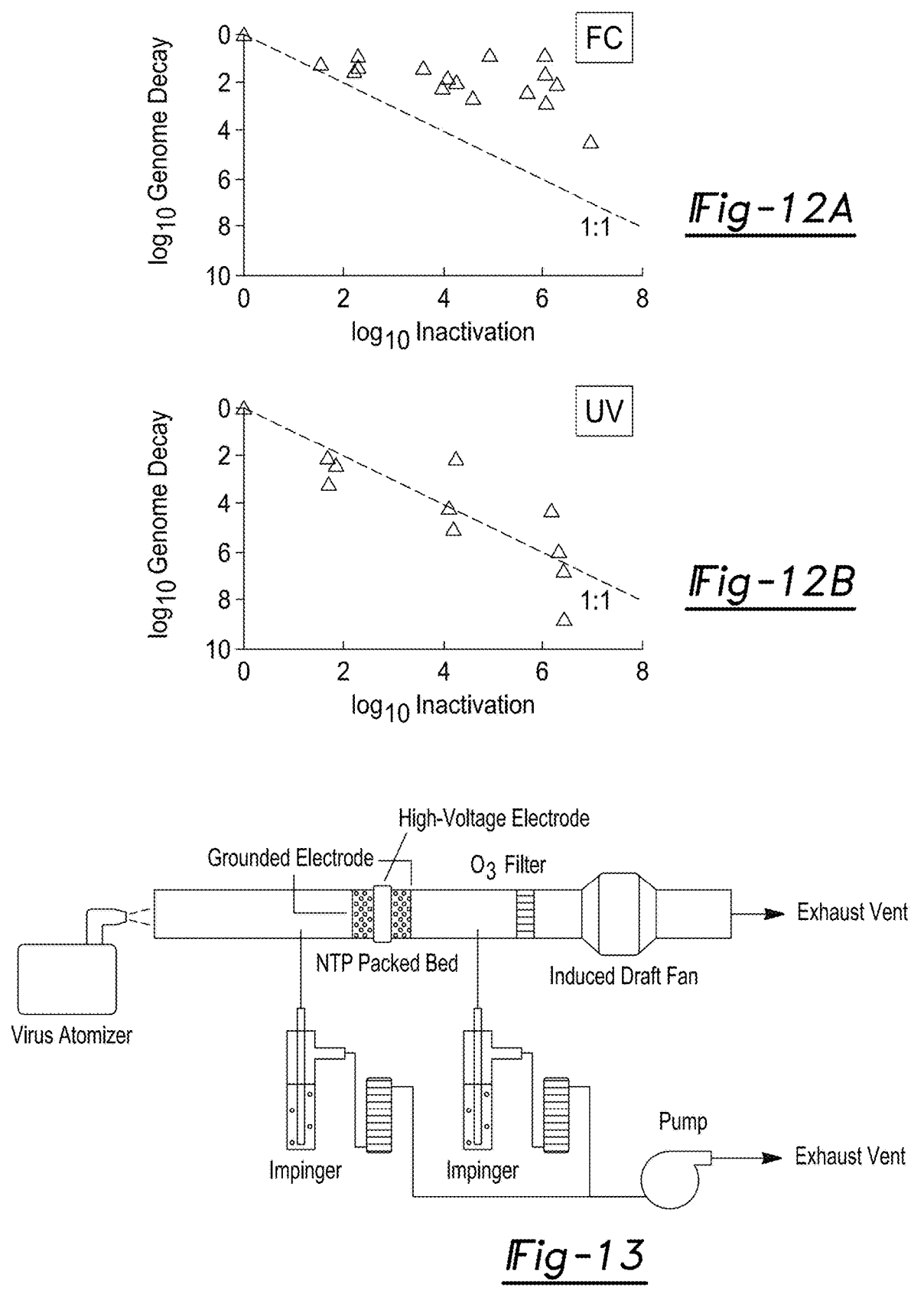
Figure 14:
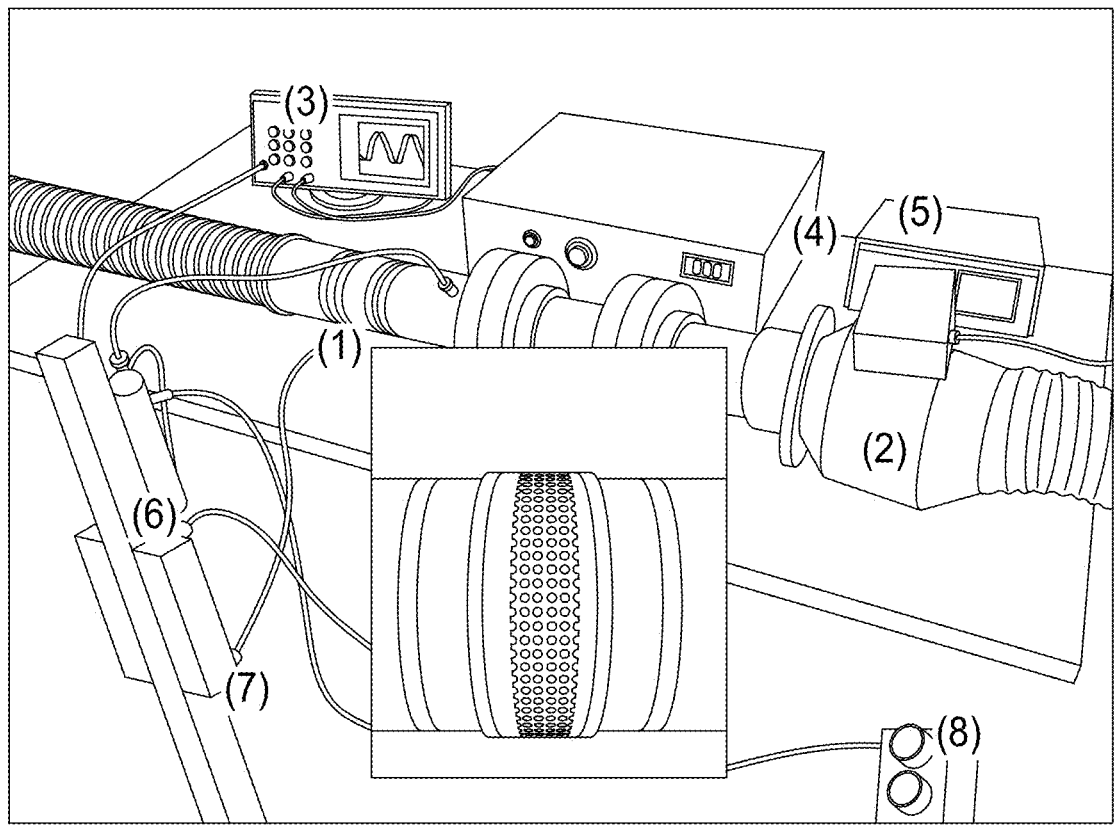
FIG. 14 is an image of an experimental non-thermal plasma NTP reactor.

FIG. 13 is a schematic of the experimental set-up depicted in FIG. 14. The reactor consists of a 3.75" diameter Plexiglas tube, a 2" section of which is packed with 500 ¼" diameter quartz beads sandwiched between and encircled by brass mesh electrodes energized up to ±30 kV AC by a 60 Hz power supply. To examine the effect of reactive radicals such as O., OH−, OH. on viral aerosols, liquid solutions containing the target virus are aerosolized into the airstreams, up to 330 slpm, supplied to the reactor. After the liquid component of the droplets evaporates, the remaining viral aerosols in air are carried through the NTP reactor. Identical upstream and downstream impingers operating under identical conditions draw air samples at 1 slpm from the pre- and post- NTP-treatment airstreams, capturing a portion of viral aerosols in the impinger liquid. After plating and culturing the collected virus samples with the host *E.coli* cells, plaque assays are conducted and the results reported as pfu/ml for each impinger sample. Separate samples from each impinger undergo quantitative polymerase chain reaction (qPCR) analyses to measure the relative abundance of the viral genome, whether infective or not, upstream and downstream of the reactor, on which basis the filtration efficiency of the reactor is calculated. Inactivation rate or efficiency is determined from the overall reduction in infective virus (based on plaque assay) less the reduction due to electrostatic and physical filtration of the aerosols in the reactor. An aerosol particle counter can be provided to physically measure aerosol filtration within the NTP reactor to complement the current approach which uses qPCR to determine filtration based on changes in the abundance of genome copies. Because qPCR analyses involve amplification of a small fragment of the complete genome, damage caused by exposure to oxidants has the potential to cause gene copy counts for the samples collected after exposure to bias low. Particle counts can serve as a correction to this bias.

Figure 15:
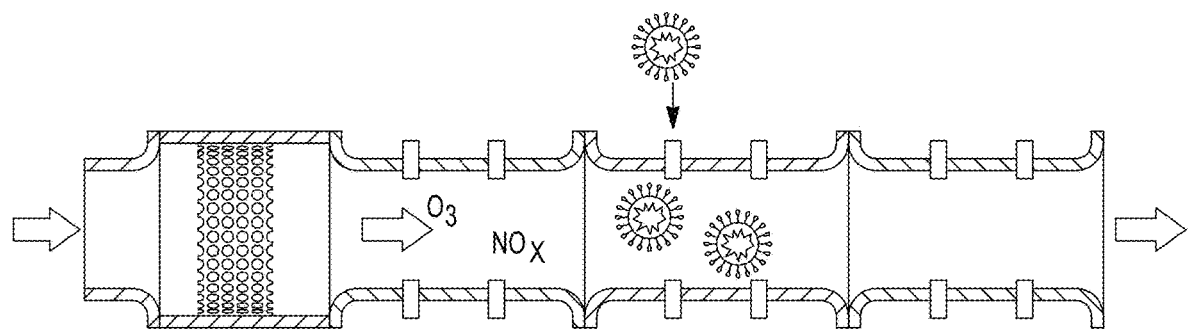
FIG. 15 is a schematic of existing NTP reactor and modular reactor extension for studying inactivation kinetics of airborne pathogens.
Figure 16A:
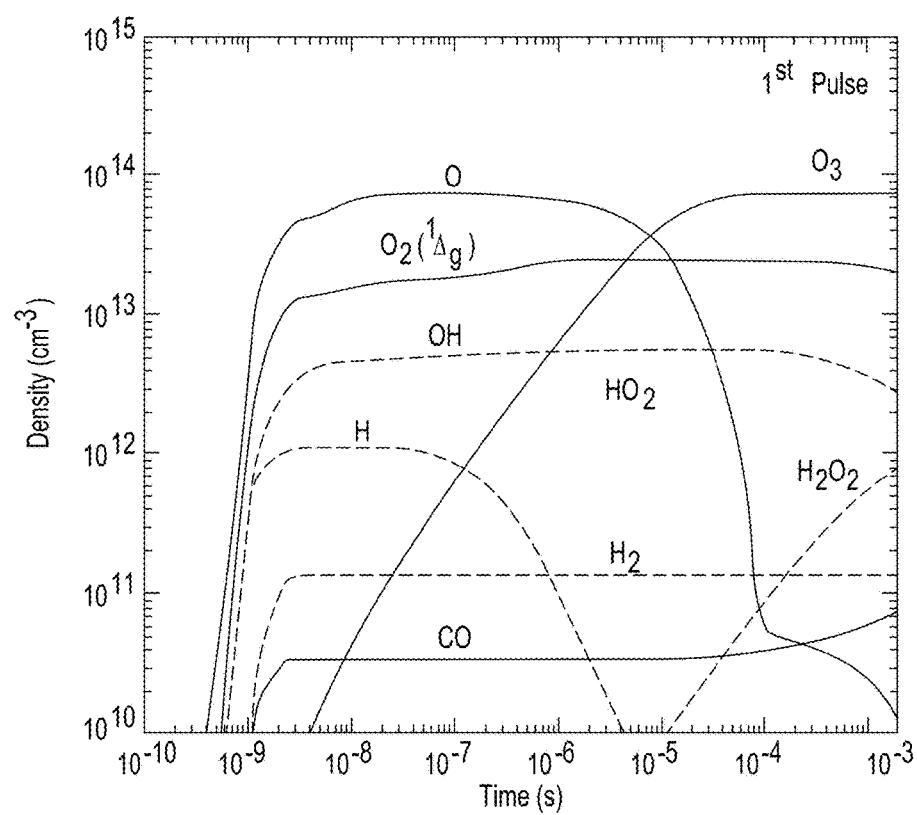
Figure 16B:
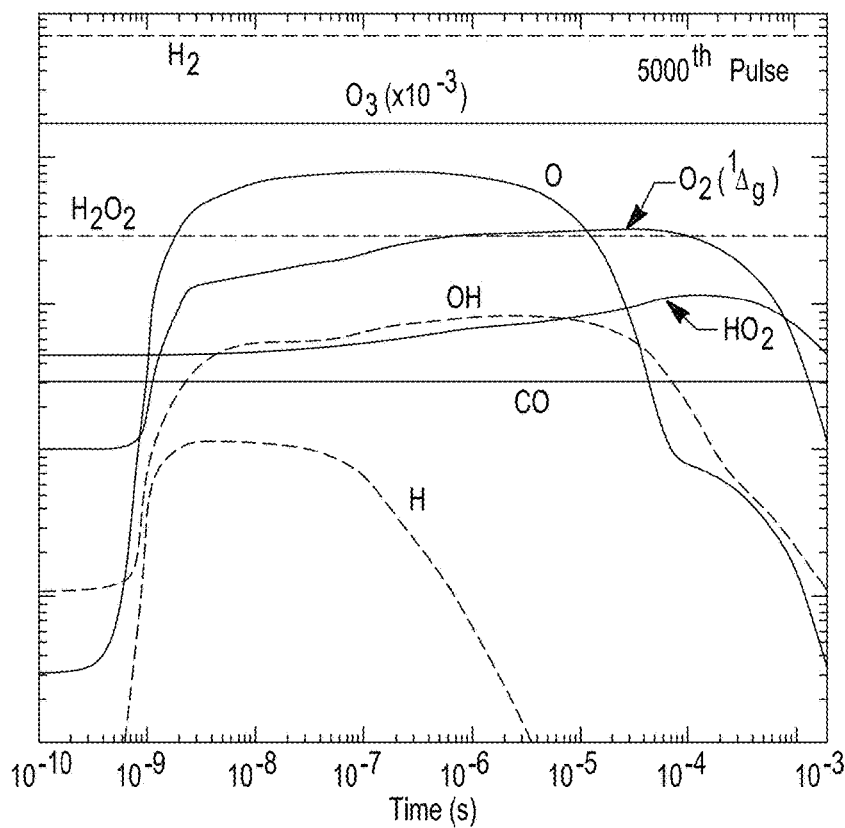
Figure 16C:
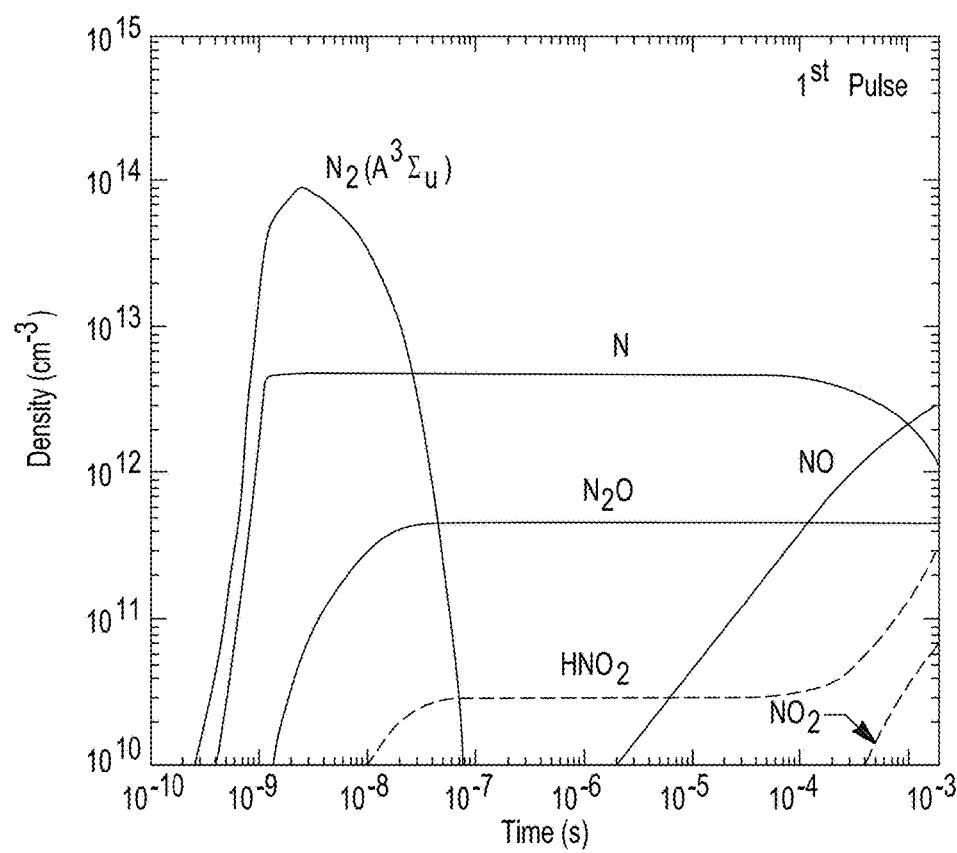
Figure 16D:
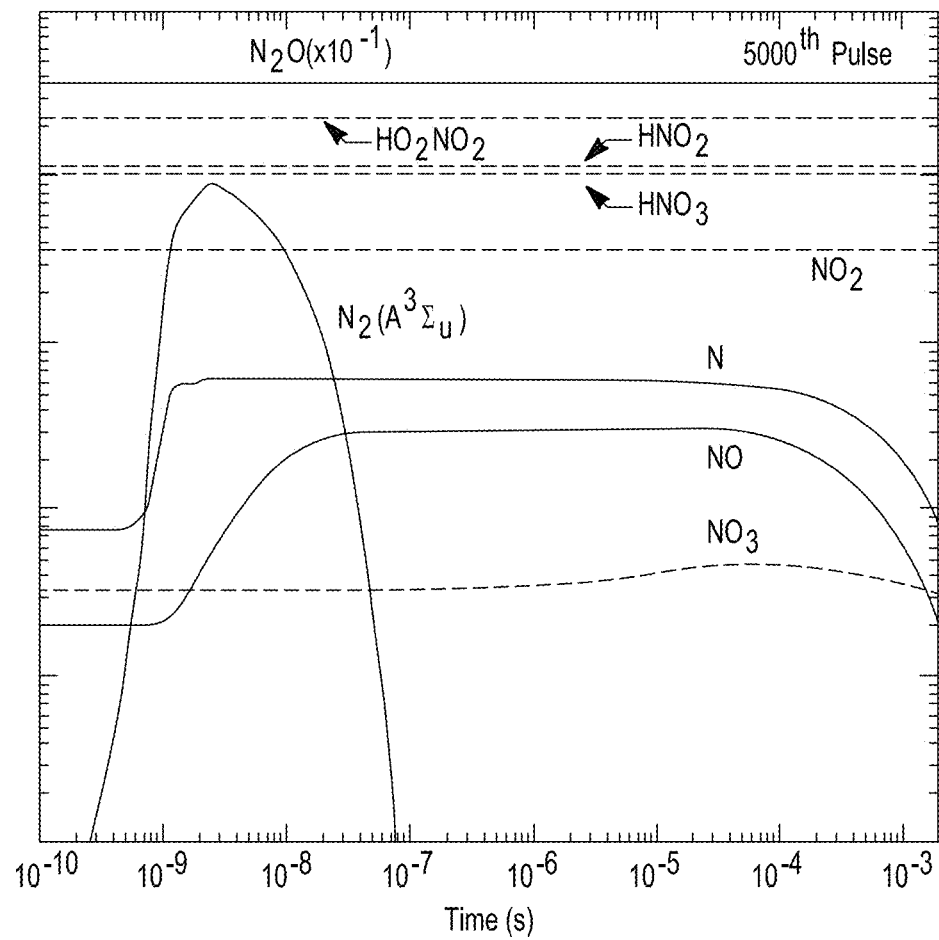

To examine the effect of ozone (O3) on viral aerosols, the airborne pathogen is introduced downstream of the energized section of the existing NTP reactor, in a modular reactor extension (FIG. 15) where longer-lived, weaker oxidants evolved from the plasma such as NOx and $O_3$ persist. A residence time of 2 sec can be achieved in a 3.4 m-long extension at a nominal 171 slpm reactor flow rate. We have measured $O_3$ concentrations as high as 4 ppm downstream of the NTP reactor, variable based on applied NTP power and air flow rate (ozone filters were used to prevent $O_3$ interference in the results shown in FIG. 8). Following sampling and collection from any of the multiple sampling ports in the extension, analysis follows protocols previously described involving thrice 10× dilutions followed by plating and plaque assay. Due to much faster reaction rates for radicals and ions, their concentrations are expected to fall rapidly beyond the energized plasma section and contribute little to airborne pathogen inactivation in the reactor extension.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of producing an immune-response-stimulating aerosol from an infectious aerosol, the method comprising:
   generating a non-thermal plasma or stable electrical discharge; and
   exposing the infectious aerosol to the non-thermal plasma or stable electrical discharge, the exposure being sublethal such that the infectious aerosol becomes inactivated while retaining sufficient information to stimulate an immune response in a host.

2. The method according to claim 1 wherein the non-thermal plasma is provided by a system having an input for receiving the infectious aerosol, and a non-thermal plasma or stable electrical discharge system for said generating the non-thermal plasma or stable electrical discharge.

3. The method according to claim 1 wherein the generating the non-thermal plasma or stable electrical discharge comprises introducing a gas mixture within a tube member and exposing the gas mixture to an electrode to generate the non-thermal plasma or stable electrical discharge.

4. A system for producing an immune-response-stimulating aerosol from an infectious aerosol, the system comprising:
- an input for receiving the infectious aerosol; and
- a non-thermal plasma or stable electrical discharge system configured to expose the infectious aerosol to sub-lethal levels such that the infectious aerosol becomes inactivated while retaining sufficient information to stimulate an immune response in a host.

5. The system according to claim 4, further comprising:
- a tube member having a gas input, the gas input configured to receive a mixture of gases; and
- an electrode disposed about the tube member, the electrode configured to generate the non-thermal plasma.

6. The system according to claim 5 wherein the non-thermal plasma extends beyond an end of the tube member.

7. The system according to claim 4 wherein the non-thermal plasma has an optical emission spectrum from 200 to 800 nm.

\* \* \* \* \*